(12) United States Patent
Connolly et al.

(10) Patent No.: US 9,126,906 B2
(45) Date of Patent: *Sep. 8, 2015

(54) ASYMMETRIC SYNTHETIC PROCESSES FOR THE PREPARATION OF AMINOSULFONE COMPOUNDS

(71) Applicant: CELGENE CORPORATION, Summit, NJ (US)

(72) Inventors: Terrence J. Connolly, Warwick, NY (US); Alexander L. Ruchelman, Cream Ridge, NJ (US); William W. Leong, Westfield, NJ (US)

(73) Assignee: Celgene Corporation, Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/772,242

(22) Filed: Feb. 20, 2013

(65) Prior Publication Data

US 2013/0217919 A1 Aug. 22, 2013

Related U.S. Application Data

(60) Provisional application No. 61/601,480, filed on Feb. 21, 2012, provisional application No. 61/648,521, filed on May 17, 2012.

(51) Int. Cl.

| C07C 215/00 | (2006.01) |
|---|---|
| C07C 315/00 | (2006.01) |
| C07C 317/00 | (2006.01) |
| C07C 315/04 | (2006.01) |
| C07B 53/00 | (2006.01) |

(52) U.S. Cl.
CPC ............... *C07C 315/04* (2013.01); *C07B 53/00* (2013.01); *C07B 2200/07* (2013.01)

(58) Field of Classification Search
None
See application file for complete search history.

(56) References Cited

U.S. PATENT DOCUMENTS

| 5,932,749 | A | 8/1999 | Anzalone et al. | |
|---|---|---|---|---|
| 6,121,184 | A * | 9/2000 | Druliner et al. | 502/159 |
| 8,981,117 | B2 * | 3/2015 | Connolly et al. | 548/472 |
| 2010/0168475 | A1 * | 7/2010 | Saindane et al. | 564/340 |

FOREIGN PATENT DOCUMENTS

| CA | 2761845 A1 | 11/2010 |
|---|---|---|
| WO | 2009158308 A1 | 12/2009 |

OTHER PUBLICATIONS

Hsiao et al. J. Am. Chem. Soc. 2004, 126, 9918-9919.*
Wilkinson et al. Organic Process Research & Development, 2002, 6, 146-148).*
Seyden-Penne Reduction by the Alumino and Borohydrides in Organic Synthesis 2nd Ed. 1997 p. 130-131.*
Burk et al., "Enantioselective hydrogenation of the C=N group: a catalytic asymmetric reductive amination procedure," J. Am. Chem. Soc., 114:6266-6267 (1992).
Corey et al., "A stable and easily prepared catalyst for the enantioselective reduction of ketones. Applications to multistep syntheses," J. Am. Chem. Soc., 109:7925-7926 (1987).
Hsiao et al., "Highly efficient synthesis of β-amino acid derivatives via asymmetric hydrogenation of unprotected enamines," J. Am. Chem. Soc., 126:9918-9919 (2004).
Armstrong et al., "Catalytic enantioselctive alkene epoxidation using novel spirocyclic N-carbethoxy-azabicyclo [3.2.1]octanones," Tetrahedron, 66:6309-6320 (2010).
Barrow et al., "A facile three-step synthesis of 1,2-amino alcohols using Ellman homochiral tert-butylsulfinamide," Tetrahedron Lett., 42:2051-2054 (2001).
Bertus et al., "General synthesis of chiral β-hydroxy sulfones via enantioselective ruthenium-catalyzed hydrogenation," Tetrahedron Lett., 40:3175-3178 (1999).
Burk et al., "A catalyst for efficient and highly enantioselective hydrogenation of aromatic, heteroaromatic, and α,β-unsaturated ketones," Org. Lett., 2:4173-4176 (2000).
Chinchilla et al., "Lipase-catalysed resolution of hydroxy sulfones," Tetrahedron: Asymmetry, 1:575-578 (1990).
Cho et al., "Efficient synthesis of optically active β-hydroxy p-tolylsulfones with very high enantiomeric excess via CBS-oxazaborolidine-catalyzed borane reduction," Tetrahedron: Asymmetry, 12:2043-2047 (2001).
Clausen et al., "Identification of ammonium chloride as an effective promoter of the asymmetric hydrogenation of a β-enamine amide," Org. Proc. Res. Dev., 10:723-726 (2006).
Desai, "Sitagliptin manufacture: a compelling tale of green chemistry, process intensification, and industrial asymmetric catalysis," Angew. Chem. Int. Ed., 50:1974-1976 (2011).
Doucet et al., "trans-[RuCl2(phosphane)2(1,2-diamine)] and chiral trans-[RuCl2(diphosphane)(1,2-diamine): shelf-stable precatalysts for the rapid, productive, and stereoselective hydrogenation of ketones," Angew. Chem. Int. Ed., 37:1703-1707 (1998).
Ellman et al., "N-tert butanesulfinyl imines: versatile intermediates for the asymmetric synthesis of amines," Acc. Chem. Res., 35:984-995 (2002).
Fryzuk et al., "Mixed donor ligands based on sp2-hybridized nitrogen donors: asymmetric hydrosilylation catalyzed by rhodium complexes that contain the 2-(2-oxazolin-2-ylmethyl)pryridine system," Tetrahedron: Asymmetry, 9:3191-3202 (1998).
Gotor et al., "Enantioselective bioreduction of β-keto sulfones with the fungus *Curvularia lunata*," Tetrahedron: Asymmetry, 12:513-515 (2001).
Han et al., "A new and direct asymmetric synthesis of a hindered chiral amine via a novel sulfinate ketimine derived from N-tosyl-1,2,3-oxathiazolidine-2-oxide: practical asymmetric synthesis of (R)-sibutramine," Org. Proc. Res. Dev., 10:327-333 (2006).
Hansen et al., "Highly efficient asymmetric synthesis of sitagliptin," J. Am. Chem. Soc., 131:8798-8804 (2009).
Hashiguchi et al., "Asymmetric transfer hydrogenation of aromatic ketones catalyzed by chiral ruthenium(II) complexes," J. Am. Chem. Soc., 117:7562-7563 (1995).
Hirao et al., "Synthesis of secondary and tertiary carbinamines from N-(trimethylsilysl)-imines and organolithium reagents," Synthesis, 461-462 (1982).
Hou et al., "Enantioselective hydrogenation of N-H imines," J. Am. Chem. Soc., 131:9882-9883 (2009).

(Continued)

*Primary Examiner* — Clinton Brooks
(74) *Attorney, Agent, or Firm* — Jones Day

(57) ABSTRACT

Processes for synthesizing aminosulfone compounds are provided. The processes provided herein utilize asymmetric reduction reactions, e.g., asymmetric hydrogenation, of protected or unprotected enamine or ketone substrates. Aminosulfone compounds obtained using methods provided herein are useful in production or synthesis of sulfone group containing isoindoline based compounds.

43 Claims, No Drawings

(56) References Cited

OTHER PUBLICATIONS

Jacobsen et al., "Asymmetric mannich-type reactions for the synthesis of aspartic acid derivatives from chiral N-tert-butanesulfinylimino esters," J. Org. Chem., 68:7112-7114 (2003).

Ji et al., "Mesoporous silica supported unsymmetric chiral Mn(III) salen complex: synthesis, characterization and effect of pore size on catalytic performance," J. Inorg. Organomet. Polym., 20:675-683 (2010).

Knowles, "Asymmetric hydrogenations," Angew. Chem. Int. Ed., 41:1998-2007 (2002).

Liu et al., "Catalytic asymmetric synthesis of tert-butanesulfinamide. Application of the asymmetric synthesis of amines," J. Am. Chem. Soc., 119:9913-9914 (1997).

Man et al., "Discovery of (S)-N-{2-[1-(3-Ethoxy-4-methoxy-phenyl)-2-methanesulfonylethyl]-1,3-dioxo-2,3-dihydro-1H-isoindol-4-yl}acetamide (Apremilast), a potent and orally active phosphodiesterase 4 and tumor necrosis factor-α inhibitor," J. Med. Chem., 52:1522-1524 (2009).

Noyori et al., "Asymmetric hydrogenation of β-keto carboxylic esters. A practical, purely chemical access to β-hydroxy esters in high enantiomeric purity," J. Am. Chem. Soc., 109:5856-5858 (1987).

Noyori, "Asymmetric catalysis: science and opportunities," Angew. Chem. Int. Ed., 41:2008-2022 (2002).

Ohkuma et al., "Asymmetric hydrogenation of alkenyl, cyclopropyl, and aryl ketones. RuCl2(xylbinap)(1,2-diamine) as a precatalyst exhibiting a wide scope," J. Am. Chem. Soc., 120:13529-13530 (1998).

Ojima et al., "New and efficient approaches to the semisynthesis of taxol and its C-13 side chain analogs by means of β-lactam synthon method," Tetrahedron, 34:6985-7012 (1992).

Roberts, "Preparative biotransformations," J. Chem. Soc., Perkin Trans., 1:1-21 (1999).

Allwein et al., "Efficient synthesis of chiral phenethylamines: preparation, asymmetric hydrogenation, and mild deprotection of ene-trifluoroacetamides," Tetrahedron Lett., 47:6409-6412 (2006).

Scherkenbeck et al., "Model studies directed toward forskolin: synthesis of a tricyclic model compound from farwesol," Tetrahedron, 44:6325-6336 (1988).

Servi et al., "Baker's yeast as a reagent in organic synthesis," Synthesis, 1-25 (1990).

Steinhuebel et al., "Direct asymmetric reductive amination," J. Am. Chem. Soc., 131:11316-11317 (2009).

Tang et al., "Asymmetric synthesis of β-amino acid derivatives incorporating a broad range of substitution patterns by enolate additions to tert-butanesulfinyl imines," J. Org. Chem., 67:7819-7832 (2002).

Tang et al., "The tert-butanesulfinyl group: an ideal chiral directing group and boc-surrogate for the asymmetric synthesis and applications of β-amino acids," J. Org. Chem., 64:12-13 (1999).

Tobe et al., "Paracyclophanedodecynes C36H8 and C36Cl8: the smallest paracyclophynes and their transformation into the carbon cluster ion C36," Angew. Chem. Int. Ed., 40:4072-4074 (2001).

Vogl et al., "Towards perfect asymmetric catalysis: additives and cocatalysts," Angew. Chem. Int. Ed., 38:1570-1577 (1999).

Wan et al., "An efficient synthesis of chiral β-hydroxy sulfones via ru-catalyzed enantioselective hydrogenation in the presence of iodine," Org. Lett., 9:5613-5616 (2007).

Ward et al., "High-yield biocatalytic amination reactions in organic synthesis," Curr. Org. Chem. 14:1914-1927 (2010).

Xie et al., "Transition metal-catalyzed enantioselective hydrogenation of enamines and imines," Chem. Rev. 111:1713-1760 (2011).

Yu et al., "A concise synthesis of homochiral sedaminese and related alkaloids. A new reductive application of Jacobsen's catalyst," Tetrahedron Letters, 40:6665-6668 (1999).

Zhao et al., "Enantioselective reduction of β-keto sulfones using the NaBH4/Me3SiCl system catalyzed by polymer-supported chiral sulfonamide," Tetrahedron: Asymmetry, 13:2095-2098 (2002).

Xu et al., "Asymmetric Hydrogenation of Ketones Using a Ruthenium(II) Catalyst Containing BINOL-Derived Monodonor Phosphorus-Donor Ligands," Org. Lett. 6:4105-4107 (2004).

Hayashi, "Rhodium-catalyzed asymmetric addition of aryl- and alkenylboron reagents to electron-deficient olefins," Pure Appl. Chem. 76(3):465-475 (2004).

Yoshida et al., "A New cine-Substitution of Alkenyl Sulfones with Aryltitanium Reagents Catalyzed by Rhodium: Mechanistic Studies and Catalytic Asymmetric Synthesis of Allylarenes," J. Am. Chem. Soc. 125:2872-2873 (2003).

\* cited by examiner

ASYMMETRIC SYNTHETIC PROCESSES FOR THE PREPARATION OF AMINOSULFONE COMPOUNDS This application claims priority to U.S. Provisional Application No. 61/601,480, filed Feb. 21, 2012, and U.S. Provisional Application No. 61/648,521, filed May 17, 2012, the entireties of which are incorporated herein by reference.

1. FIELD

Provided herein are processes for the preparation of an aminosulfone compound, e.g., (S)-2-(3-ethoxy-4-methoxyphenyl)-1-(methanesulfonyl)-eth-2-ylamine. The compound can be used in making sulfone containing PDE 4 modulators, for example, (S)—N-(2-(1-(3-ethoxy-4-methoxyphenyl)-2-(methylsulfonyl)ethyl)-1,3-dioxoisoindolin-4-yl)acetamide and (S)—N-(2-(1-(3-ethoxy-4-methoxyphenyl)-2-(methylsulfonyl)ethyl)-3-oxoisoindolin-4-yl)cyclopropanecarboxamide.

2. BACKGROUND

Enhanced or unregulated production of tumor necrosis factor α (TNF-α) has been implicated in inflammatory, allergic, and autoimmune diseases. It has been shown that adenosine 3',5'-cyclic monophosphate (cAMP) plays a role in TNF-α production. Elevation of cAMP in inflammatory leukocytes inhibits their activation and the subsequent release of inflammatory mediators, including TNF-α. The primary cellular mechanism for the inactivation of cAMP is the breakdown of cAMP by a family of isoenzymes referred to as cyclic nucleotide phosphodiesterases (PDE). The inhibition of PDE, in particular type IV PDE (PDE4), is effective in the inhibition of TNF-α release.

For example, 2-[1-(3-ethoxy-4-methoxyphenyl)-2-methylsulfonylethyl]-4-acetylaminoisoindoline-1,3-dione is a PDE4 inhibitor that is currently under investigation as an anti-inflammatory for the treatment of a variety of conditions, including asthma, chronic obstructive pulmonary disease, psoriasis and other allergic, autoimmune and rheumatologic conditions. S-enantiomer form of 2-[1-(3-ethoxy-4-methoxyphenyl)-2-methylsulfonylethyl]-4-acetylaminoisoindoline-1,3-dione can be prepared by reacting (S)-aminosulfone 1 with intermediate 2.

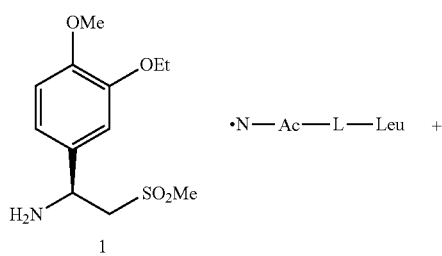

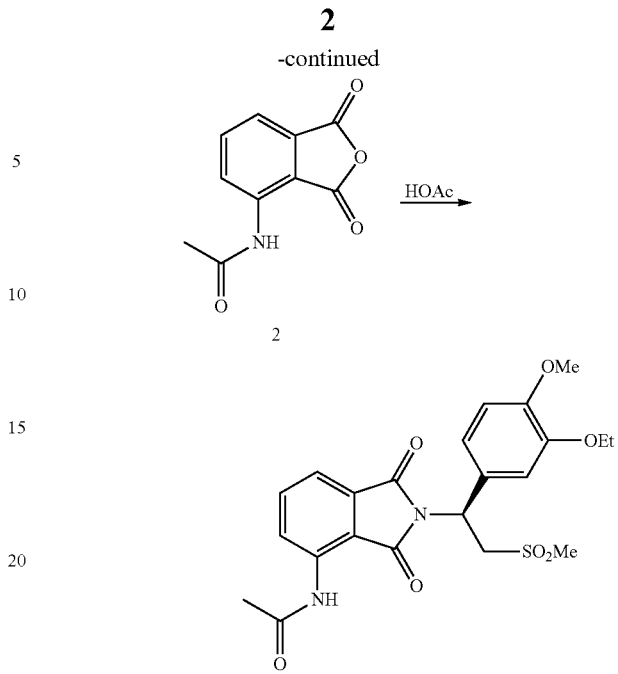

Existing methods for synthesizing (S)-aminosulfone 1 involve resolution of the corresponding racemic aminosulfone by techniques known in the art. Examples include the formation and crystallization of chiral salts, and the use of chiral high performance liquid chromatography. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions* p. 268 (E. L. Eliel, Ed., Univ. of Notre Dame Press, Notre Dame, In., 1972). In one example, as depicted in Scheme 1 below, (S)-aminosulfone 1 is prepared by resolution of racemic aminosulfone 3 with N—Ac-L-Leu. Racemic aminosulfone 3 is prepared by converting 3-ethoxy-4-methoxybenzonitrile 4 to enamine intermediate 5 followed by enamine reduction and borate hydrolysis. This process has been reported in U.S. Patent Application Publication No. 2010/0168475.

Scheme 1

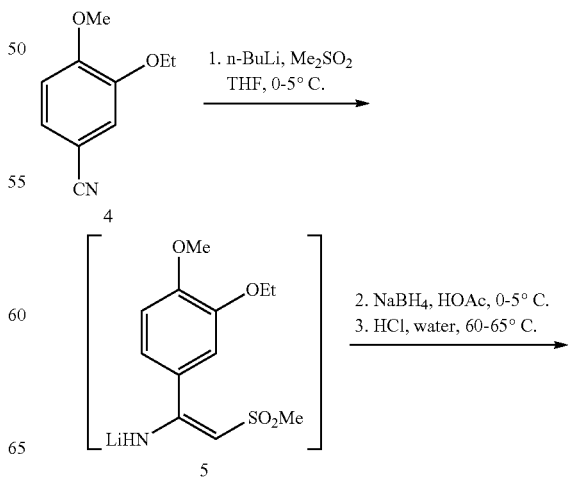

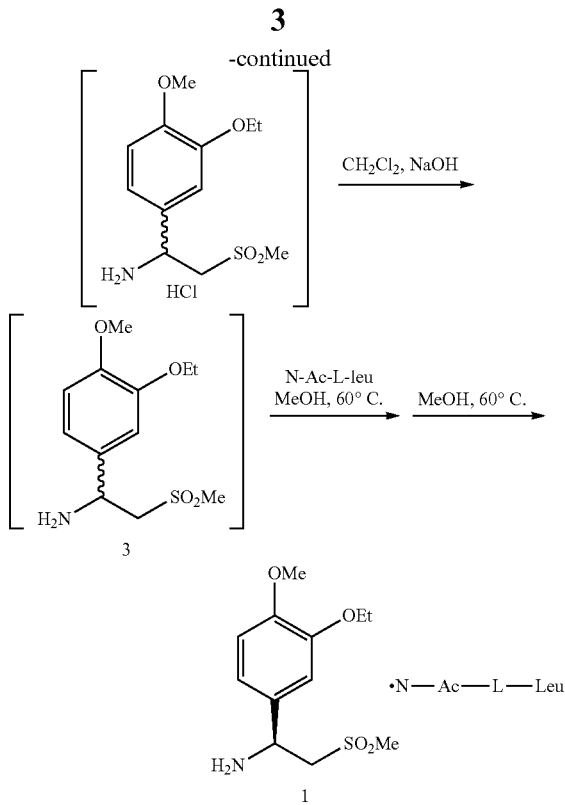

The procedure for preparing an enantiomerically enriched or enantiomerically pure aminosulfone, such as compound 1, may be inefficient because it involves the resolution of racemic aminosulfone 3. Thus, a need exists as to asymmetric synthetic processes for the preparation of an enantiomerically enriched or enantiomerically pure aminosulfone, particularly for manufacturing scale production. Direct catalytic asymmetric hydrogenation of a suitable enamine or ketone intermediate is of particular interest because it eliminates the need for either classic resolution or the use of stoichiometric amount of chiral auxiliary, and thus, may be synthetically efficient and economical.

3. SUMMARY

Provided herein are processes for the preparation of enantiomerically enriched or enantiomerically pure aminosulfone compounds. In one embodiment, provided is a process for the preparation of an enantiomerically enriched or enantiomerically pure aminosulfone compound of Formula (I):

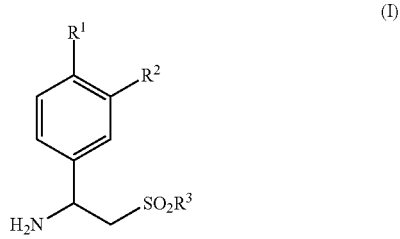

or a salt, solvate including a hydrate, stereoisomer, isotopologue, or polymorph thereof, wherein $R^1$, $R^2$, and $R^3$ are defined herein elsewhere.

In one embodiment, provided herein are processes for the preparation of aminosulfones comprising the step of reducing an enamine, or a salt thereof, via hydrogenation in the presence of (1) a metal catalyst and a chiral ligand, or (2) a chiral metal catalyst/ligand complex.

In another embodiment, provided herein are processes for the preparation of aminosulfones comprising the steps of: (a) reacting an enamine, or a salt thereof, with an acylating reagent to form an N-acyl enamine; (b) reducing the N-acyl enamine via hydrogenation in the presence of (1) a metal catalyst and a chiral ligand, or (2) a chiral metal catalyst/ligand complex to form an N-acyl aminosulfone; and (c) converting the N-acyl aminosulfone to the aminosulfone.

In yet another embodiment, provided herein are processes for the preparation of aminosulfones comprising the steps of: (a) reacting a ketone with ammonia or an ammonium salt to form an enamine; (b) optionally isolating the enamine; and (c) reducing the enamine via hydrogenation in the presence of (1) a metal catalyst and a chiral ligand, or (2) a chiral metal catalyst/ligand complex.

In yet another embodiment, provided herein are processes for the preparation of aminosulfones comprising the steps of: (a) reducing a ketone via hydrogenation in the presence of (1) a metal catalyst and a chiral ligand, or (2) a chiral metal catalyst/ligand complex to form a hydroxysulfone; and (b) converting the hydroxysulfone to the aminosulfone.

In yet another embodiment, provided herein are processes for the preparation of aminosulfones comprising the steps of: (a) reducing a ketone via transfer hydrogenation in the presence of a transfer reagent and (1) a metal catalyst and a chiral ligand, or (2) a chiral metal catalyst/ligand complex to form a hydroxylsulfone; and (b) converting the hydroxysulfone to the aminosulfone.

In yet another embodiment, provided herein are processes for the preparation of aminosulfones comprising the steps of: (a) reducing a ketone via borane reduction in the presence of a borane reagent and a chiral oxazaborolidine to form a hydroxylsulfone; and (b) converting the hydroxysulfone to the aminosulfone.

In yet another embodiment, provided herein are processes for the preparation of aminosulfones comprising the steps of: (a) reducing a ketone in the presence of a reducing reagent, a Lewis acid, and a polymer-supported chiral sulfonamide to form a hydroxylsulfone; and (b) converting the hydroxysulfone to the aminosulfone.

In yet another embodiment, provided herein are processes for the preparation of aminosulfones comprising the steps of: (a) reducing a ketone via yeast or fungus-mediated asymmetric reduction in the presence of a yeast or fungus to form a hydroxylsulfone; and (b) converting the hydroxysulfone to the aminosulfone.

In yet another embodiment, provided herein are processes for the preparation of aminosulfones comprising the steps of: (a) reducing a ketone via hydrosilylation in the presence of a silane and (1) a metal catalyst and a chiral ligand, or (2) a chiral metal catalyst/ligand complex to form a hydroxylsulfone; and (b) converting the hydroxysulfone to the aminosulfone.

In yet another embodiment, provided herein are processes for the preparation of aminosulfones comprising the steps of: (a) contacting a hydroxysulfone with a lipase and an ester to form an enantiomerically enriched hydroxylsulfone; and (b) converting the enantiomerically enriched hydroxysulfone to the aminosulfone.

In yet another embodiment, provided herein are processes for the preparation of aminosulfones comprising the steps of: (a) reacting a ketone with an N-acyl hydrazine; (b) reducing the resulting compound from step (a) via hydrogenation in the presence of (1) a metal catalyst and a chiral ligand, or (2) a chiral metal catalyst/ligand complex; and (c) converting the resulting compound from step (b) to the aminosulfone.

In yet another embodiment, provided herein are processes for the preparation of aminosulfones comprising the step of reducing an enamine, or a salt thereof, via borane reduction in the presence of a borane reagent and a chiral ligand.

4. DETAILED DESCRIPTION

4.1 Definition

As used herein and unless otherwise indicated, the term "process(es)" provided herein refers to the methods disclosed herein which are useful for preparing a compound provided herein. Modifications to the methods disclosed herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive groups or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, a reaction that is "substantially complete" or is driven to "substantial completion" means that the reaction contains more than about 80% by percent yield, in one embodiment more than about 90% by percent yield, in another embodiment more than about 95% by percent yield, and in another embodiment more than about 97% by percent yield of the desired product.

As used herein, and unless otherwise indicated, the term "salt" includes, but is not limited to, salts of acidic or basic groups that may be present in the compounds disclosed herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise indicated, the term "hydrate" means a compound or a salt thereof, that further includes a stoichiometric or non-stoichiometeric amount of water bound by non-covalent intermolecular forces.

As used herein, and unless otherwise indicated, the term "solvate" means a solvate formed from the association of one or more solvent molecules to a compound. The term "solvate" includes hydrates (e.g., mono-hydrate, dihydrate, trihydrate, tetrahydrate, and the like).

As used herein, and unless otherwise indicated, the term "polymorph" means solid crystalline forms of a compound or complex thereof. Different polymorphs of the same compound can exhibit different physical, chemical and/or spectroscopic properties.

As used herein, and unless otherwise indicated, the term "halo", "halogen", or the like means —F, —Cl, —Br, or —I.

As used herein, and unless otherwise indicated, the term "alkyl" means a saturated, monovalent, unbranched or branched hydrocarbon chain. Examples of alkyl groups include, but are not limited to, ($C_1$-$C_6$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl. Longer alkyl groups include heptyl, octyl, nonyl and decyl groups. An alkyl group can be unsubstituted or substituted with one or more suitable substituents. The alkyl groups may also be isotopologues of the natural abundance alkyl groups by being enriched in isotopes of carbon and/or hydrogen (i.e., deuterium or tritium).

As used herein, and unless otherwise indicated, the term "alkoxy" means an alkyl group that is linked to another group via an oxygen atom (i.e., —O-alkyl). An alkoxy group can be unsubstituted or substituted with one or more suitable substituents. Examples of alkoxy groups include, but are not limited to, ($C_1$-$C_6$)alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-t-butyl, —O-pentyl, —O-isopentyl, —O-neopentyl and —O-hexyl. The alkoxy groups may also be isotopologues of the natural abundance alkoxy groups by being enriched in isotopes of carbon, oxygen and/or hydrogen (i.e., deuterium or tritium).

As used herein, and unless otherwise indicated, the term "alcohol" means any compound substituted with an —OH group. The alcohol group may also be isotopologues of the natural abundance alcohol groups by being enriched in isotopes of oxygen and/or hydrogen (i.e., deuterium or tritium).

As used herein, and unless otherwise indicated, the term "amino" or "amino group" means a monovalent group of the formula —$NH_2$, —NH(alkyl), —NH(aryl), —N(alkyl)$_2$, —N(aryl)$_2$ or —N(alkyl)(aryl). The amino groups may also be isotopologues of the natural abundance amino groups by being enriched in isotopes of carbon, nitrogen and/or hydrogen (i.e., deuterium or tritium).

Unless otherwise indicated, the compounds provided herein, including intermediates useful for the preparation of the compounds provided herein, which contain reactive functional groups (such as, without limitation, carboxy, hydroxy, and amino moieties) also include protected derivatives thereof "Protected derivatives" are those compounds in which a reactive site or sites are blocked with one or more protecting groups (also known as blocking groups). Suitable protecting groups for carboxy moieties include benzyl, t-butyl, and the like as well as isotopologues of the like. Suitable protecting groups for amino and amido groups include acetyl, trifluoroacetyl, t-butyloxycarbonyl, benzyloxycarbonyl, and the like. Suitable protecting groups for hydroxy include benzyl and the like. Other suitable protecting groups are well known to those of ordinary skill in the art. The choice and use of protecting groups and the reaction conditions to install and remove protecting groups are described in T. W. Green, *Protective Groups in Organic Synthesis* (Third Ed., Wiley, New York, 1999), which is incorporated herein by reference in its entirety.

As used herein, and unless otherwise indicated, acronyms or symbols for groups or reagents have the following definition: HPLC=high performance liquid chromatography; TFA=trifluoroacetic acid; TFE=2,2,2-trifluoroethanol, THF=tetrahydrofuran; CH$_3$CN=acetonitrile; HOAc=acetic acid; DCM=dichloromethane.

As used herein, and unless otherwise indicated, the term "substituted" or "substitution," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; deuterium, halo; haloalkyl (e.g., trifluoromethyl); heterocloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., CONH$_2$); substituted carbamyl (e.g., CONH-alkyl, CONH-aryl, CONH-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., SO$_2$NH$_2$); substituted sulfonamido; thiol; alkylthio; arylthio; arylalkylthio; cycloalkylthio; heterocyclothio; alkylthiono; arylthiono; and arylalkylthiono. In some embodiments, a substituent itself may be substituted with one or more chemical moieties such as, but not limited to, those described herein.

As used herein, and unless otherwise indicated, the term "about" is used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

If the stereochemistry of a structure or a portion thereof is not indicated, e.g., with bold or dashed lines, the structure or portion thereof is to be interpreted as encompassing all enantiomerically pure, enantiomerically enriched, diastereomerically pure, diastereomerically enriched, and racemic mixtures of the compounds.

Unless otherwise indicated, the terms "enantiomerically enriched" and "enantiomerically pure," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, and even such as at least 80% by weight. In some embodiments, the enrichment can be much greater than 80% by weight, providing a "substantially optically enriched," "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, and such as at least 95% by weight. In some embodiments, the enantiomerically enriched composition has a higher potency with respect to therapeutic utility per unit mass than does the racemic mixture of that composition.

As used herein, and unless otherwise indicated, the term "hydrogenation" refers to a chemical process that adds hydrogen atom to an unsaturated bond.

The disclosure can be understood more fully by reference to the following detailed description and illustrative examples, which are intended to exemplify non-limiting embodiments.

Although most embodiments and examples provided herein are directed to the (S)-enantiomer of an aminosulfone compound, it is to be understood that the corresponding (R)-enantiomer of an aminosulfone compound can be prepared by the disclosed processes when the stereochemistry of chiral reactant, reagent, solvent, catalyst, ligand or the like is reversed.

4.2 Processes

Provided herein are processes for the preparation of enantiomerically enriched or enantiomerically pure aminosulfone compounds. In some embodiments, the processes provided herein utilize asymmetric hydrogenation.

The enantiomerically enriched or enantiomerically pure aminosulfone compounds are useful for the preparation of certain sulfone group containing compounds. In one embodiment, the sulfone group containing compound is (S)—N-(2-(1-(3-ethoxy-4-methoxyphenyl)-2-(methylsulfonyl)ethyl)-1,3-dioxoisoindolin-4-yl)acetamide, or isotopologues thereof. In another embodiment, the sulfone group containing compound is (S)—N-(2-(1-(3-ethoxy-4-methoxyphenyl)-2-(methylsulfonyl)ethyl)-3-oxoisoindolin-4-yl)cyclopropanecarboxamide, or isotopologues thereof.

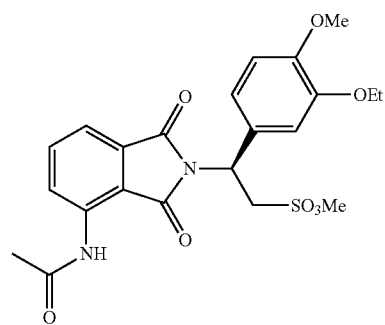

(S)-N-(2-(1-(3-ethoxy-4-methoxyphenyl)-2-
(methylsulfonyl)ethyl)-1,3-dioxoisoindolin-4-yl)
acetamide

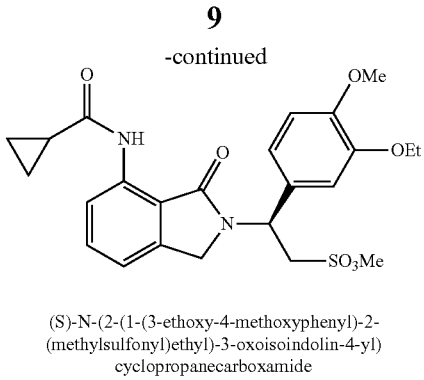

(S)-N-(2-(1-(3-ethoxy-4-methoxyphenyl)-2-
(methylsulfonyl)ethyl)-3-oxoisoindolin-4-yl)
cyclopropanecarboxamide 4.2.1 Asymmetric Hydrogenation of an Enamine Substrate In one embodiment, the processes provided herein utilize asymmetric hydrogenation of an enamine substrate, as illustrated in Scheme 2 below.

Scheme 2

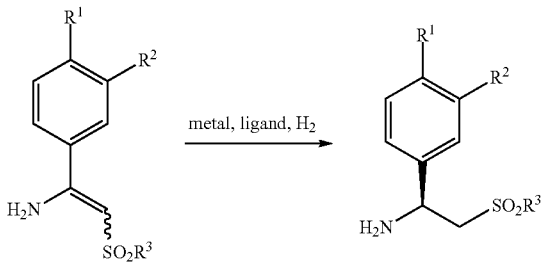

In one embodiment, provided is a process for preparing an aminosulfone compound of Formula (I):

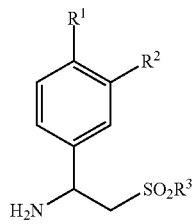

(I)

or a salt, solvate including a hydrate, isotopologue, or polymorph thereof, wherein $R^1$ and $R^2$ are each independently hydrogen, halogen, substituted or unsubstituted ($C_1$-$C_6$) alkyl, substituted or unsubstituted ($C_1$-$C_6$)alkoxy, ($C_3$-$C_{18}$) cycloalkyl, ($C_3$-$C_6$)cycloalkoxy, cyano, —$CF_3$, or ($C_3$-$C_{18}$) cycloalkyl-($C_1$-$C_6$)alkoxy, or an isotopologue thereof; and $R^3$ is ($C_1$-$C_6$)alkyl, or an isotopologue thereof;

comprising the step of reducing an enamine of Formula (II):

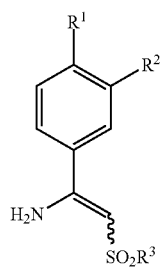

(II)

or a salt or isotopologue thereof, via hydrogenation in the presence of (1) a metal catalyst and a chiral ligand, or (2) a chiral metal catalyst/ligand complex.

In one embodiment, the hydrogenation is conducted with hydrogen gas.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted ($C_1$-$C_6$)alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In one embodiment, the hydrogenation occurs to an enamine of Formula (II) in free base form. In another embodiment, the hydrogenation occurs to an enamine of Formula (II) in a salt form. In one embodiment, the hydrogenation occurs to an enamine of Formula (II) in hydrochloride salt form.

The metal catalyst can be any metal catalyst that is capable of promoting hydrogenation. In one embodiment, the metal catalyst contains a metal such as, but not limited to, copper, nickel, palladium, platinum, rhodium, iridium, and ruthenium. In one embodiment, the metal catalyst contains rhodium. In another embodiment, the metal catalyst contains ruthenium. In yet another embodiment, the metal catalyst contains iridium. In one embodiment, the metal catalyst is Rh(cod)$_2$OTf. In another embodiment, the metal catalyst is Rh(cod)$_2$BF$_4$. In yet another embodiment, the metal catalyst is [Ir(cod)Cl]$_2$.

The chiral ligand or chiral metal catalyst/ligand complex can be any chiral ligand or chiral metal catalyst/ligand complex that is capable of promoting asymmetric hydrogenation. In one embodiment, the chiral ligand or chiral metal catalyst/ligand complex is, but not limited to, (S,R)-t-Bu Josiphos, Josiphos SL-J011-2, (S,S)-Me-Duphos, (S,S)-Chiraphos, (R)-Phanephos, (R)—Ru(OAc)$_2$(DM-segphos), [(R,R)-Me-BPE]Rh(cod)BF$_4$, (R)—C$_3$-TunePhos, (R)—[Rh(cod) TCFP]BF$_4$, or a stereoisomer thereof. In one embodiment, the chiral ligand is (S,R)-t-Bu Josiphos or Josiphos SL-J011-2. In one embodiment, the chiral ligand is (S,R)-t-Bu Josiphos. In another embodiment, the chiral ligand is Josiphos SL-J011-2. In another embodiment, the chiral ligand is (R,S)-t-Bu Josiphos.

The hydrogenation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

The molar ratio of the chiral ligand to the metal catalyst can be any ratio that is capable of promoting hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

The hydrogenation can occur under a hydrogen pressure between about 1 psia and about 550 psia. In general, the higher the hydrogen pressure, the shorter is the reaction time. In one embodiment, the hydrogen pressure is between about 15 psig and about 250 psig. In one embodiment, the hydrogen pressure is between about 15 psig and about 90 psig. In another embodiment, the hydrogen pressure is between about 90 psig and about 250 psig. In one embodiment, the hydrogen pressure is about 15 psig. In another embodiment, the hydrogen pressure is about 90 psig. In yet another embodiment, the hydrogen pressure is about 250 psig.

The hydrogenation can occur in a solvent such as, but not limited to, ethyl acetate, diethyl ether, tetrahydrofuran, 1,4-dioxane, acetonitrile, dichloromethane, chloroform, N-methyl pyrrolidinone, N,N-dimethyl-formamide, dimethyl sulfoxide, formic acid, acetic acid, methanol, ethanol, isopropanol, 2,2,2-trifluoroethanol, and mixtures thereof. In one embodiment, the solvent is ethanol. In another embodiment, the solvent is 2,2,2-trifluoroethanol.

The reaction temperature can be between about 10° C. and about 90° C. In one embodiment, the reaction temperature is between about 40° C. and about 60° C. In one embodiment, the reaction temperature is about 50° C.

The reaction time can vary from about 1 to about 72 hours, depending on the reaction temperature and the hydrogen pressure. In general, the higher the reaction temperature and the higher the hydrogen pressure, the shorter is the reaction time. In one embodiment, the reaction time is about 18 hours where the reaction temperature is about 50° C. In one embodiment, the reation time is about one to about two hours where the reaction temperature if about 50° C. and the hydrogen pressure is about 90 psig. In another embodiment, the reation time is about seven hours where the reaction temperature if about 50° C. and the hydrogen pressure is about 30 psig.

In one embodiment, the asymmetric hydrogenation of an enamine of Formula (II), or a salt thereof, wherein $R^1$ is OMe, $R^2$ is OEt, and $R^3$ is Me, occurs in 2,2,2-trifluoroethanol, in the presence of about 1 mol % of Rh(cod)$_2$OTf and about 1 mol % of (R,S)-t-Bu Josiphos, under a hydrogen pressure of about 90 psig, at about 50° C.

In one embodiment, the asymmetric hydrogenation of an enamine of Formula (II), or a salt thereof, wherein $R^1$ is OMe, $R^2$ is OEt, and $R^3$ is Me, occurs in 2,2,2-trifluoroethanol, in the presence of about 0.5 mol % of Rh(cod)$_2$OTf and about 0.5 mol % of (S,R)-t-Bu Josiphos, under a hydrogen pressure of about 90 psig, at about 50° C.

In another embodiment, the asymmetric hydrogenation of a hydrochloride salt of an enamine of Formula (II), wherein $R^1$ is OMe, $R^2$ is OEt, and $R^3$ is Me, occurs in 2,2,2-trifluoroethanol, in the presence of (1) a metal catalyst and a chiral ligand, or (2) a chiral metal catalyst/ligand complex, under a hydrogen pressure of about 90 psig, at about 50° C.

All of the combinations of the above embodiments are encompassed by this invention.

4.2.2 Asymmetric Hydrogenation of an N-Acyl Enamine Substrate

In one embodiment, the processes provided herein utilize asymmetric hydrogenation of an N-acyl enamine substrate, as illustrated in Scheme 3 below.

Scheme 3

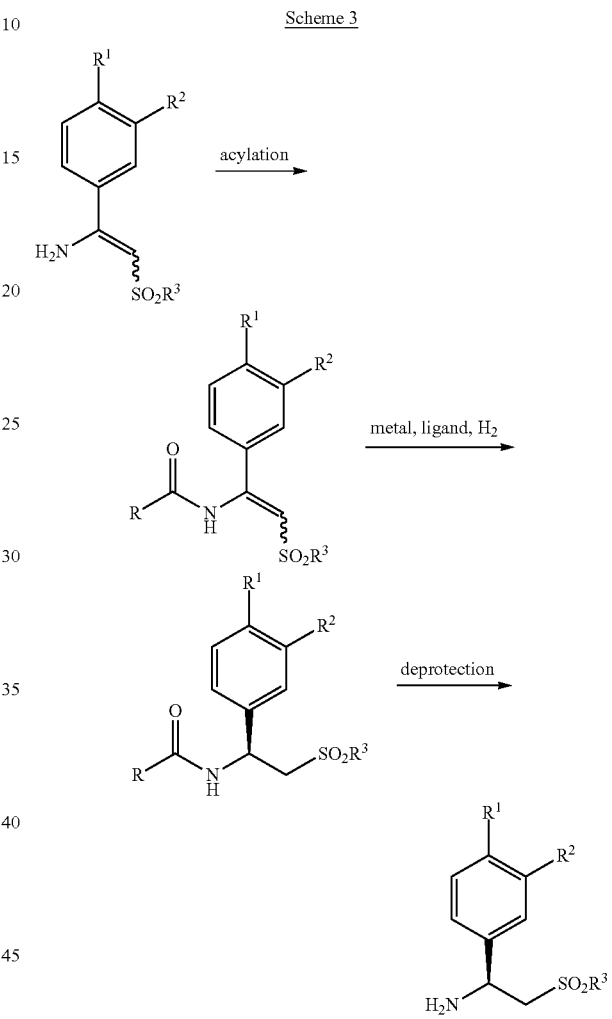

In one embodiment, provided is a process for preparing an aminosulfone compound of Formula (I):

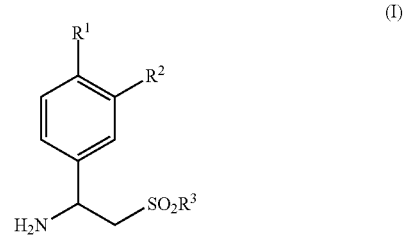

(I)

or a salt, solvate including a hydrate, isotopologue, or polymorph thereof, wherein $R^1$ and $R^2$ are each independently hydrogen, halogen, substituted or unsubstituted ($C_1$-$C_6$) alkyl, substituted or unsubstituted ($C_1$-$C_6$)alkoxy, ($C_3$-$C_{18}$)

cycloalkyl, $(C_3-C_6)$cycloalkoxy, cyano, —$CF_3$, or $(C_3-C_{18})$ cycloalkyl-$(C_1-C_6)$alkoxy, or an isotopologue thereof; and $R^3$ is $(C_1-C_6)$alkyl, or an isotopologue thereof;
comprising the steps of
(a) reacting an enamine of Formula (II):

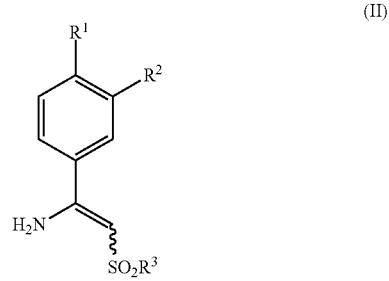

(II)

or a salt or isotopologue thereof, with an acylating reagent to form an N-acyl enamine of Formula (III):

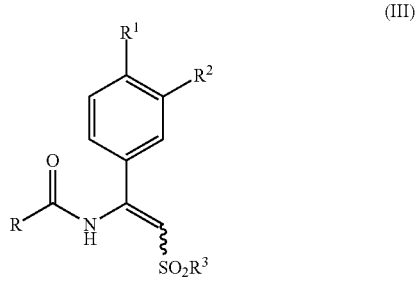

(III)

or an isotopologue thereof, wherein R is hydrogen; $(C_1-C_6)$ alkyl, itself optionally substituted with one or more halogen; or 5 to 10 membered aryl or heteroaryl, optionally substituted with one or more halogen; or an isotopologue thereof;
(b) reducing the N-acyl enamine of Formula (III), or an isotopologue thereof, via hydrogenation in the presence of (1) a metal catalyst and a chiral ligand, or (2) a chiral metal catalyst/ligand complex to form an N-acyl aminosulfone of Formula (IV):

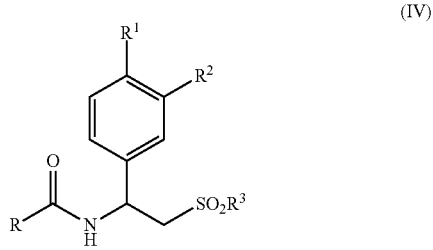

(IV)

or an isotopologue thereof; and
(c) converting the N-acyl aminosulfone of Formula (IV), or an isotopologue thereof, to the aminosulfone of Formula (I), or a salt or isotopologue thereof.

In one embodiment, the hydrogenation is conducted with hydrogen gas.

The general techniques for protecting and deprotecting an amino group, as those utilized in step (a) and (c) are known in the art. See generally, T. W. Green, *Protective Groups in Organic Synthesis* (Third Ed., Wiley, New York, 1999). One selection criteria for R, among other things, is the ease of removal of the acyl group in step (c) in order to preserve the stereochemistry of the carbon atom to which the nitrogen atom is attached.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In one embodiment, R is $(C_1-C_6)$alkyl, itself optionally substituted with one or more halogen, or an isotopologue thereof. In one embodiment, R is $CF_3$, or an isotopologue thereof.

In step (a), the acylating reagent may be any suitable acylating reagent known in the art. In one embodiment, the acylating reagent is trifluoroacetic anhydride. In another embodiment, the acylating reagent is trifluoroacetyl chloride.

In step (a), the acylation of the enamine of Formula (II), or a salt thereof, can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is dichloromethane.

In step (a), the reaction temperature can be between about −10° C. and about 90° C. In one embodiment, the reaction temperature is about 0° C.

In step (b), the metal catalyst can be any metal catalyst that is capable of promoting hydrogenation. In one embodiment, the metal catalyst contains a metal such as, but not limited to, copper, nickel, palladium, platinum, rhodium, iridium, and ruthenium. In one embodiment, the metal catalyst contains rhodium. In another embodiment, the metal catalyst contains ruthenium. In yet another embodiment, the metal catalyst contains iridium. In one embodiment, the metal catalyst is $Rh(cod)_2OTf$. In another embodiment, the metal catalyst is $Rh(cod)_2BF_4$. In yet another embodiment, the metal catalyst is $[Ir(cod)Cl]_2$.

In step (b), the chiral ligand or chiral metal catalyst/ligand complex can be any chiral ligand or chiral metal catalyst/ligand complex that is capable of promoting asymmetric hydrogenation. In one embodiment, the chiral ligand or chiral metal catalyst/ligand complex is, but not limited to, (S,R)-t-Bu Josiphos, (S,S)-Me-Duphos, (S,S)-Chiraphos, (R)-Phanephos, (S)-(DM-Segphos), [(R,R)-Me-BPE]Rh(cod)BF$_4$, (R)—C$_3$-TunePhos, (R)—[Rh(cod)TCFP]BF$_4$, (S)—N-benzyl-N-methyl-MonoPhos, or a stereoisomer thereof. In one embodiment, the chiral ligand is (R,R)-Me-Duphos.

In step (b), the hydrogenation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

In step (b), the molar ratio of the chiral ligand to the metal catalyst can be any ratio that is capable of promoting hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

In step (b), the hydrogenation can occur under a hydrogen pressure between about 1 psia and about 550 psia. In general, the higher the hydrogen pressure, the shorter is the reaction time. In one embodiment, the hydrogen pressure is between about 15 psig and about 250 psig. In one embodiment, the hydrogen pressure is between about 15 psig and about 90 psig. In another embodiment, the hydrogen pressure is between about 90 psig and about 250 psig. In one embodiment, the hydrogen pressure is about 15 psig. In another embodiment, the hydrogen pressure is about 90 psig. In yet another embodiment, the hydrogen pressure is about 250 psig.

In step (b), the hydrogenation can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is ethanol. In another embodiment, the solvent is 2,2,2-trifluoroethanol.

In step (b), the reaction temperature can be between about 10° C. and about 90° C. In one embodiment, the reaction temperature is between about 40° C. and about 60° C. In one embodiment, the reaction temperature is about 50° C. In another embodiment, the reaction temperature is about 35° C.

In step (b), the reaction time can vary from about 1 to about 72 hours, depending on the reaction temperature and the hydrogen pressure. In general, the higher the reaction temperature and the higher the hydrogen pressure, the shorter is the reaction time. In one embodiment, the reaction time is about 18 hours where the reaction temperature is about 50° C.

In one embodiment, the asymmetric hydrogenation of an N-acyl enamine of Formula (III), wherein $R^1$ is OMe, $R^2$ is OEt, $R^3$ is Me, and R is $CF_3$, occurs in 2,2,2-trifluoroethanol, in the presence of about 2 mol % of $Rh(cod)_2OTf$ and about 3 mol % of (R,R)-Me-Duphos, under a hydrogen pressure of about 90 psig, at about 35° C.

In another embodiment, the asymmetric hydrogenation of an N-acyl enamine of Formula (III), wherein $R^1$ is OMe, $R^2$ is OEt, $R^3$ is Me, and R is $CF_3$, occurs in 2,2,2-trifluoroethanol, in the presence of about 5 mol % of $Rh(cod)_2OTf$ and about 10 mol % of (S,S)-Me-Duphos, under a hydrogen pressure of about 250 psig, at about 50° C.

In yet another embodiment, the asymmetric hydrogenation of an N-acyl enamine of Formula (III), wherein $R^1$ is OMe, $R^2$ is OEt, $R^3$ is Me, and R is $CF_3$, occurs in 2,2,2-trifluoroethanol, in the presence of about 1 mol % of $Rh(cod)_2OTf$ and about 2 mol % of (R,R)-Me-Duphos, under a hydrogen pressure of between about 90 psig and about 250 psig, at about 25° C.

In yet another embodiment, the asymmetric hydrogenation of an N-acyl enamine of Formula (III), wherein $R^1$ is OMe, $R^2$ is OEt, $R^3$ is Me, and R is $CF_3$, occurs in 2,2,2-trifluoroethanol, in the presence of about 1 mol % of $Rh(cod)_2OTf$ and about 2 mol % of (S,S)-Me-Duphos, under a hydrogen pressure of about 250 psig, at about 50° C.

In step (c), the removal of the acyl group in the N-acyl aminosulfone of Formula (IV) can occur in the presence of a base. In one embodiment, the base is $K_2CO_3$.

In step (c), the removal of the acyl group in the N-acyl aminosulfone of Formula (IV) can occur in the presence of an acid. In one embodiment, the acid is HCl.

All of the combinations of the above embodiments are encompassed by this invention.

4.2.3 Asymmetric Reductive Amination of a Ketone Substrate

In one embodiment, the processes provided herein utilize asymmetric reductive amination of a ketone substrate, as illustrated in Scheme 4 below.

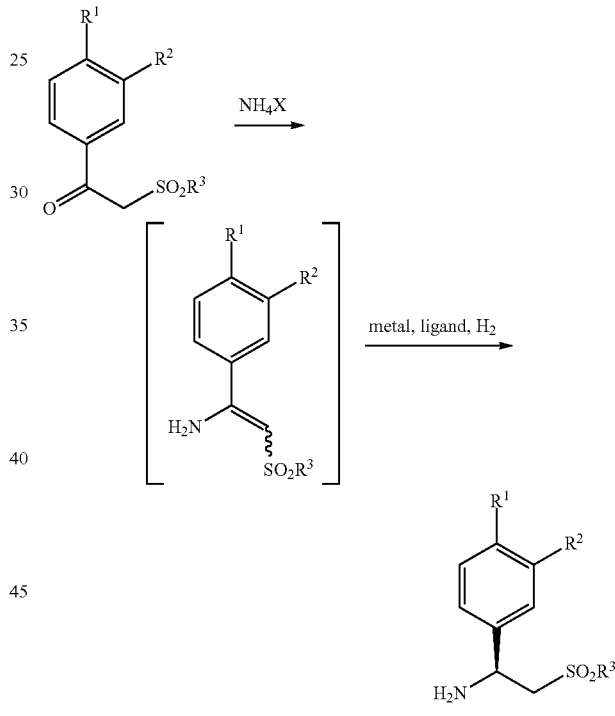

In one embodiment, provided is a process for preparing an aminosulfone compound of Formula (I):

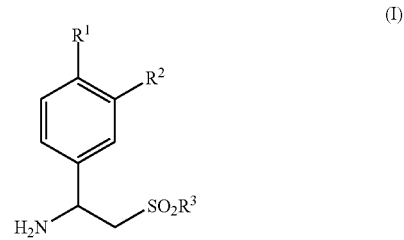

or a salt, solvate including a hydrate, isotopologue, or polymorph thereof, wherein $R^1$ and $R^2$ are each independently hydrogen, halogen, substituted or unsubstituted ($C_1$-$C_6$) alkyl, substituted or unsubstituted ($C_1$-$C_6$)alkoxy, ($C_3$-$C_{18}$) cycloalkyl, ($C_3$-$C_6$)cycloalkoxy, cyano, —$CF_3$, or ($C_3$-$C_{18}$) cycloalkyl-($C_1$-$C_6$)alkoxy, or an isotopologue thereof; and $R^3$ is ($C_1$-$C_6$)alkyl, or an isotopologue thereof;

comprising the steps of (a) reacting a ketone of Formula (V):

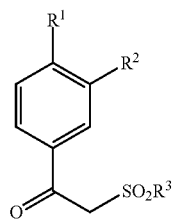

(V)

or an isotopologue thereof, with ammonia or an ammonium salt to form an enamine of Formula (II):

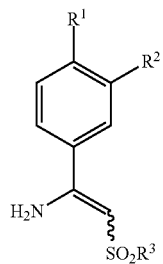

(II)

or a salt or isotopologue thereof;

(b) optionally isolating the enamine of Formula (II), or a salt or isotopologue thereof; and (c) reducing the enamine of Formula (II), or a salt or isotopologue thereof, via hydrogenation in the presence of (1) a metal catalyst and a chiral ligand, or (2) a chiral metal catalyst/ligand complex.

In one embodiment, the hydrogenation is conducted with hydrogen gas.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted ($C_1$-$C_6$)alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof and $R^3$ is Me, or an isotopologue thereof.

In one embodiment, the ammonium salt in step (a) is ammonium acetate.

In step (a), the reaction between the ketone of Formula (V) and ammonia or an ammonium salt can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is ethanol. In another embodiment, the solvent is 2,2,2-trifluoroethanol.

In step (c), the metal catalyst can be any metal catalyst that is capable of promoting hydrogenation. In one embodiment, the metal catalyst contains a metal such as, but not limited to, copper, nickel, palladium, platinum, rhodium, iridium, and ruthenium. In one embodiment, the metal catalyst contains rhodium. In another embodiment, the metal catalyst contains ruthenium. In yet another embodiment, the metal catalyst contains iridium. In one embodiment, the metal catalyst is $Rh(cod)_2OTf$. In another embodiment, the metal catalyst is $Rh(cod)_2BF_4$. In yet another embodiment, the metal catalyst is $[Ir(cod)Cl]_2$.

In step (c), the chiral ligand or chiral metal catalyst/ligand complex can be any chiral ligand or chiral metal catalyst/ligand complex that is capable of promoting asymmetric hydrogenation. In one embodiment, the chiral ligand or chiral metal catalyst/ligand complex is, but not limited to, (S,R)-t-Bu Josiphos, Josiphos SL-J011-2, (S,S)-Me-Duphos, (S,S)-Chiraphos, (R)-Phanephos, (R)—$Ru(OAc)_2$(DM-segphos), [(R,R)-Me-BPE]Rh(cod)$BF_4$, (R)—$C_3$-TunePhos, (R)—[Rh(cod)TCFP]$BF_4$, or a stereoisomer thereof. In one embodiment, the chiral ligand is (S, R)-t-Bu Josiphos or Josiphos SL-J011-2. In one embodiment, the chiral ligand is (S,R)-t-Bu Josiphos. In another embodiment, the chiral ligand is Josiphos SL-J011-2.

In step (c), the hydrogenation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

In step (c), the molar ratio of the chiral ligand to the metal catalyst can be any ratio that is capable of promoting hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

In step (c), the hydrogenation can occur under a hydrogen pressure between about 1 psia and about 550 psia. In general, the higher the hydrogen pressure, the shorter is the reaction time. In one embodiment, the hydrogen pressure is between about 15 psig and about 250 psig. In one embodiment, the hydrogen pressure is between about 15 psig and about 90 psig. In another embodiment, the hydrogen pressure is between about 90 psig and about 250 psig. In one embodiment, the hydrogen pressure is about 15 psig. In another embodiment, the hydrogen pressure is about 90 psig. In yet another embodiment, the hydrogen pressure is about 250 psig.

In step (c), the hydrogenation can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is ethanol. In another embodiment, the solvent is 2,2,2-trifluoroethanol.

In step (c), the reaction temperature can be between about 10° C. and about 90° C. In one embodiment, the reaction temperature is between about 40° C. and about 60° C. In one embodiment, the reaction temperature is about 50° C. In another embodiment, the reaction temperature is about 35° C.

In step (c), the reaction time can vary from about 1 to about 72 hours, depending on the reaction temperature and the hydrogen pressure. In general, the higher the reaction temperature and the higher the hydrogen pressure, the shorter is the reaction time. In one embodiment, the reaction time is about 18 hours where the reaction temperature is about 50° C.

In one embodiment, the enamine of Formula (II) is isolated after step (a), and the asymmetric hydrogenation of step (c) occurs in 2,2,2-trifluoroethanol, in the presence of about 0.37 mol % of Rh(cod)$_2$OTf and about 0.37 mol % of (S,R)-t-Bu Josiphos, under a hydrogen pressure of about 90 psig, at about 50° C.

In another embodiment, the enamine of Formula (II) is not isolated after step (a), and the asymmetric hydrogenation of step (c) occurs in 2,2,2-trifluoroethanol, in the presence of about 1 mol % of Rh(cod)$_2$OTf and about 1 mol % of (S,R)-t-Bu Josiphos, under a hydrogen pressure of about 90 psig, at about 50° C.

All of the combinations of the above embodiments are encompassed by this invention.

4.2.4 Asymmetric Hydrogenation of a Ketone Substrate

In one embodiment, the processes provided herein utilize asymmetric hydrogenation of a ketone substrate, as illustrated in Scheme 5 below.

Scheme 5

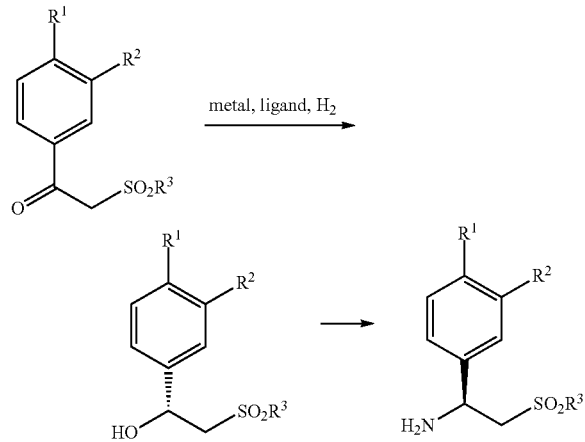

In one embodiment, provided is a process for preparing an aminosulfone compound of Formula (I):

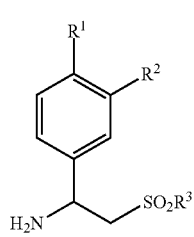

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$ alkoxy, $(C_3-C_{18})$ cycloalkyl, $(C_3-C_6)$ cycloalkoxy, cyano, —CF$_3$, or $(C_3-C_{18})$ cycloalkyl-$(C_1-C_6)$ alkoxy, or an isotopologue thereof; and $R^3$ is $(C_1-C_6)$ alkyl, or an isotopologue thereof;

comprising the steps of (a) reducing a ketone of Formula (V):

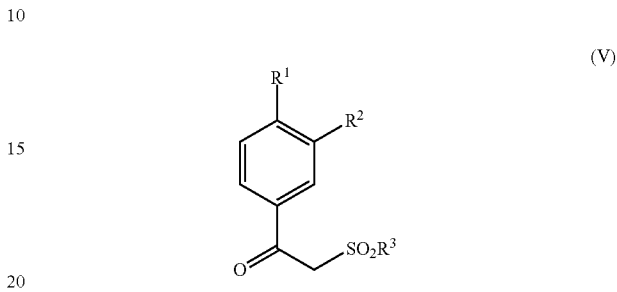

or an isotopologue thereof, via hydrogenation in the presence of (1) a metal catalyst and a chiral ligand, or (2) a chiral metal catalyst/ligand complex to form a hydroxylsulfone of Formula (VI):

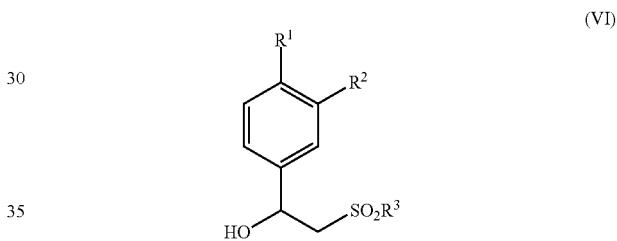

or an isotopologue thereof; and (b) converting the hydroxysulfone of Formula (VI), or an isotopologue thereof, to the aminosulfone of Formula (I), or a salt or isotopologue thereof.

In one embodiment, the hydrogenation is conducted with hydrogen gas.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$ alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof and $R^3$ is Me, or an isotopologue thereof.

In step (a), the metal catalyst can be any metal catalyst that is capable of promoting hydrogenation. In one embodiment, the metal catalyst contains a metal such as, but not limited to, copper, nickel, palladium, platinum, rhodium, iridium, and ruthenium. In one embodiment, the metal catalyst contains rhodium. In another embodiment, the metal catalyst contains ruthenium. In yet another embodiment, the metal catalyst contains iridium. In one embodiment, the metal catalyst is Rh(cod)$_2$OTf. In another embodiment, the metal catalyst is Rh(cod)$_2$BF$_4$. In yet another embodiment, the metal catalyst is [Ir(cod)Cl]$_2$. In yet another embodiment, the metal catalyst is Ru(OAc)$_2$. In yet another embodiment, the metal catalyst is RuCl$_2$. In yet another embodiment, the metal catalyst is RuCl(benzene). In yet another embodiment, the metal catalyst is RuCl(p-cymene).

In step (a), the chiral ligand or chiral metal catalyst/ligand complex can be any chiral ligand or chiral metal catalyst/ligand complex that is capable of promoting asymmetric hydrogenation. In one embodiment, the chiral ligand or chiral metal catalyst/ligand complex is, but not limited to, (S,R)-t-Bu Josiphos, Josiphos SL-J011-2, (S,S)-Me-Duphos, (S,S)-Chiraphos, (R)-Phanephos, (R)—Ru(OAc)₂(DM-segphos), [(R,R)-Me-BPE]Rh(cod)BF₄, (R)—C₃-TunePhos, (R)—[Rh(cod)TCFP]BF₄, or a stereoisomer thereof. In one embodiment, the chiral ligand is (S, R)-t-Bu Josiphos or Josiphos SL-J011-2. In one embodiment, the chiral ligand is (S,R)-t-Bu Josiphos. In another embodiment, the chiral ligand is Josiphos SL-J011-2. In one embodiment, the chiral ligand or chiral metal catalyst/ligand complex is, but not limited to, (S)—Ru(OAc)₂(BINAP), (S)—Ru(OAc)₂(DM-SEGPHOS), RuCl(p-cymene)[(S,S)-Ts-DPEN], RuCl₂—[(R)-(DM-SEGPHOS)][(R,R)-(DPEN)], RuCl₂—[(R)-(Phanephos)][(S,S)-(DPEN)], RuCl₂—[(R)-DM-BINAP][(R,R)-DPEN], or a stereoisomer thereof. In one embodiment, the chiral metal catalyst/ligand complex is RuCl(p-cymene)[(S,S)-Ts-DPEN].

In step (a), the hydrogenation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

In step (a), the molar ratio of the chiral ligand to the metal catalyst can be any ratio that is capable of promoting hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

In step (a), the hydrogenation can occur under a hydrogen pressure between about 1 psia and about 550 psia. In general, the higher the hydrogen pressure, the shorter is the reaction time. In one embodiment, the hydrogen pressure is between about 15 psig and about 450 psig. In one embodiment, the hydrogen pressure is between about 15 psig and about 90 psig. In another embodiment, the hydrogen pressure is between about 90 psig and about 250 psig. In another embodiment, the hydrogen pressure is between about 250 psig and about 450 psig. In one embodiment, the hydrogen pressure is about 15 psig. In another embodiment, the hydrogen pressure is about 90 psig. In yet another embodiment, the hydrogen pressure is about 250 psig. In yet another embodiment, the hydrogen pressure is about 450 psig.

In step (a), the hydrogenation can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is ethanol. In another embodiment, the solvent is 2,2,2-trifluoroethanol. In yet another embodiment, the solvent is isopropanol.

In step (a), the reaction temperature can be between about 10° C. and about 90° C. In one embodiment, the reaction temperature is between about 40° C. and about 60° C. In one embodiment, the reaction temperature is about 50° C. In another embodiment, the reaction temperature is about 35° C.

In step (a), the reaction time can vary from about 1 to about 72 hours, depending on the reaction temperature and the hydrogen pressure. In general, the higher the reaction temperature and the higher the hydrogen pressure, the shorter is the reaction time. In one embodiment, the reaction time is about 18 hours where the reaction temperature is about 50° C. In another embodiment, the reaction time is about 16 hours where the reaction temperature is about 50° C.

In one embodiment, step (a) occurs in the presence of an additive. In one embodiment, the additive is an amine, pyridine, pyridine N-oxide, imidazole, alkoxide, halide, or a combination thereof. In one embodiment, the amine is triethylamine, diisopropylethylamine, or 1,8-diazabicyclo[5.4.0]undec-7-ene (DBU). In one embodiment, the alkoxide is $C_{1-6}$ alkoxide. In one embodiment, the alkoxide is NaOMe, NaOEt, t-BuONa, KOMe, KOEt, t-BuOK. In one embodiment, the alkoxide is t-BuOK.

In one embodiment, the asymmetric hydrogenation of a ketone of Formula (V) occurs in 2,2,2-trifluoroethanol, in the presence of about 5 mol % of Rh(cod)₂OTf and about 10 mol % of (S,R)-t-Bu Josiphos, under a hydrogen pressure of between about 90 psig and about 250 psig, at about 50° C.

In another embodiment, the asymmetric hydrogenation of a ketone of Formula (V) occurs in 2,2,2-trifluoroethanol, in the presence of about 0.5 mol % of Rh(cod)₂OTf and about 1 mol % of (S,R)-t-Bu Josiphos, under a hydrogen pressure of between about 90 psig and about 250 psig, at about 50° C.

In yet another embodiment, the asymmetric hydrogenation of a ketone of Formula (V) occurs in isopropanol, in the presence of about 5 mol % of t-BuOK and about 1 mol % of RuCl(p-cymene)[(S,S)-Ts-DPEN], under a hydrogen pressure of 450 psig, at about 50° C.

In one embodiment, in step (b), the hydroxyl group in the hydroxysulfone of Formula (VI) is replaced by a nitrogen-based nucleophile, and the resulting product is further converted to the aminosulfone of Formula (I), or a salt thereof. In one embodiment, the nitrogen-based nucleophile is phthalimide, and step (b) is illustrated as below.

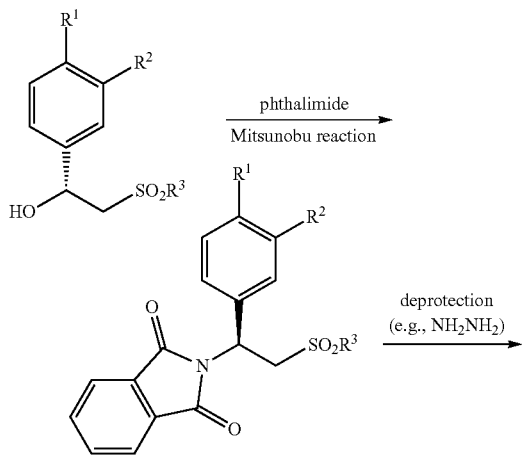

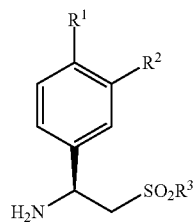

In another embodiment, the nitrogen-based nucleophile is an azide, and step (b) is illustrated as below.

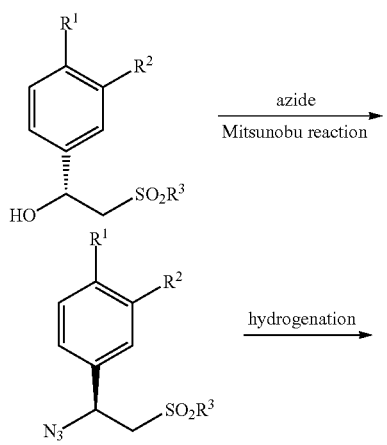

In one embodiment, the azide is hydrogen azide (i.e., hydrazoic acid), sodium azide, or potassium azide.

The Mitsunobu reaction can occur in any condition known in the art that is suitable for Mitsunobu reaction. In one embodiment, the Mitsunobu reaction occurs in the presence of $PBu_3$ and diisopropyl azodicarboxylate (DIAD).

The Mitsunobu reaction can occur in any solvent known in the art that is suitable for Mitsunobu reaction. In one embodiment, the Mitsunobu reaction occurs in a solvent such as, but not limited to, toluene, ethyl acetate, diethyl ether, tetrahydrofuran, 1,4-dioxane, acetonitrile, dichloromethane, chloroform, N-methylpyrrolidinone, dimethyl formamide, dimethyl sulfoxide, and mixtures thereof. In one embodiment, the solvent is toluene.

The reaction temperature of the Mitsunobu reaction can be between about −100° C. and about 100° C. In one embodiment, the reaction temperature is between about −60° C. and about −2° C. In one embodiment, the reaction temperature is about −60° C.

The reaction time of the Mitsunobu reaction can vary from about 1 to about 72 hours, depending on the reaction temperature. In general, the higher the reaction temperature, the shorter is the reaction time. In one embodiment, the reaction time is between about 16 hours to about 20 hours where the reaction temperature is between about −60° C. and about −2° C.

The hydrogenation of azide can occur in any condition known in the art that is suitable for hydrogenation of an azide. In one embodiment, the hydrogenation occurs in the presence of Pd/C. In one embodiment, the hydrogenation occurs in a solvent of alcohol. In one embodiment, the solvent is 2,2,2-trifluoroethanol.

In one embodiment, the hydroxyl group in the hydroxysulfone of Formula (VI) is converted to an activated form such as, but not limited to, OMs and OTs; followed by replacement by a nitrogen-based nucleophile; and the resulting product is further converted to the aminosulfone of Formula (I), or a salt thereof.

The hydroxysulfone of Formula (VI) may also be utilized directly in the preparation of sulfone group containing compounds without being converted to the aminosulfone of Formula (I). In one embodiment, provided herein are processes for preparing (S)—N-(2-(1-(3-ethoxy-4-methoxyphenyl)-2-(methylsulfonyl)ethyl)-1,3-dioxoisoindolin-4-yl)acetamide as depicted below.

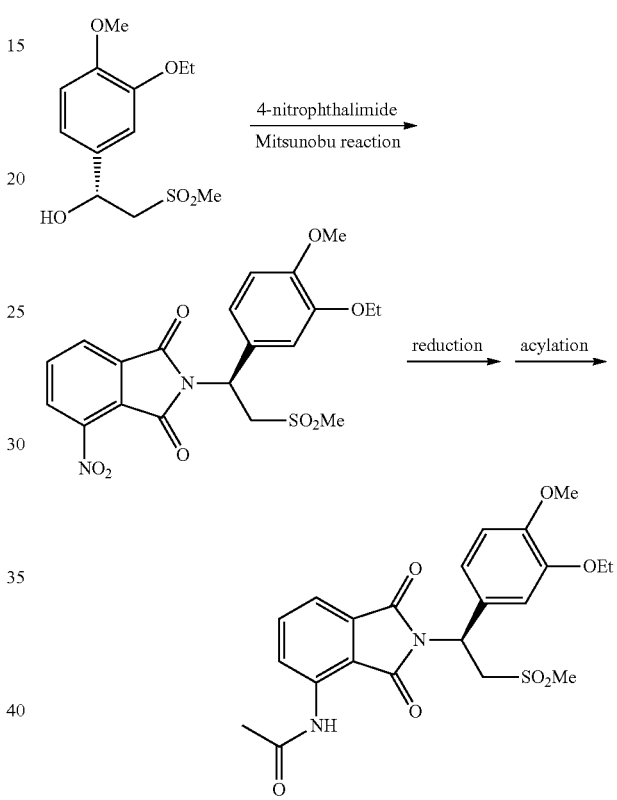

In one embodiment, provided is a process for preparing a hydroxysulfone compound of Formula (VI):

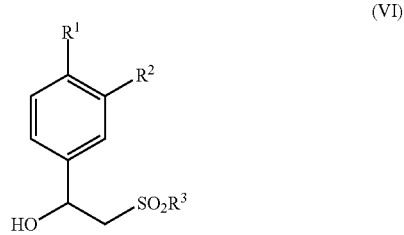

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$alkoxy, $(C_3-C_{18})$ cycloalkyl, $(C_3-C_6)$cycloalkoxy, cyano, —$CF_3$, or $(C_3-C_{18})$ cycloalkyl-$(C_1-C_6)$alkoxy, or an isotopologue thereof and $R^3$ is $(C_1-C_6)$alkyl, or an isotopologue thereof comprising the steps of (a) reducing a ketone of Formula (V):

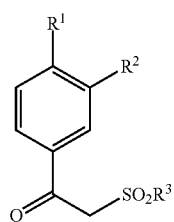

or an isotopologue thereof, via hydrogenation in the presence of (1) a metal catalyst and a chiral ligand, or (2) a chiral metal catalyst/ligand complex to form a hydroxylsulfone of Formula (VI), or an isotopologue thereof.

Step (a) is as described above and herein.

All of the combinations of the above embodiments are encompassed by this invention.

4.2.5 Asymmetric Transfer Hydrogenation of a Ketone Substrate

In one embodiment, the processes provided herein utilize asymmetric transfer hydrogenation of a ketone substrate, as illustrated in Scheme 6 below.

Scheme 6

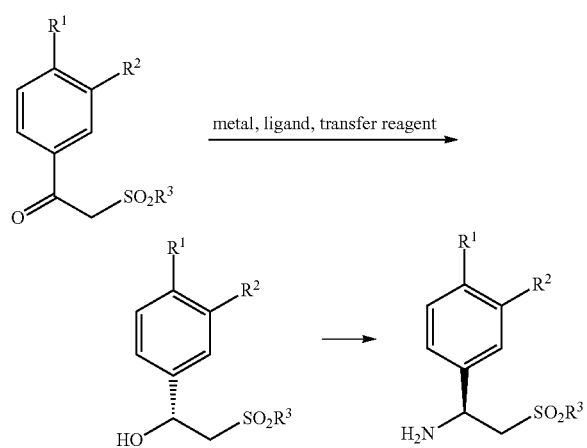

In one embodiment, provided is a process for preparing an aminosulfone compound of Formula (I):

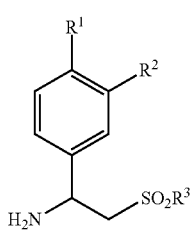

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$alkoxy, $(C_3-C_{18})$ cycloalkyl, $(C_3-C_6)$cycloalkoxy, cyano, —$CF_3$, or $(C_3-C_{18})$ cycloalkyl-$(C_1-C_6)$alkoxy, or an isotopologue thereof; and $R^3$ is $(C_1-C_6)$alkyl, or an isotopologue thereof;

comprising the steps of (a) reducing a ketone of Formula (V):

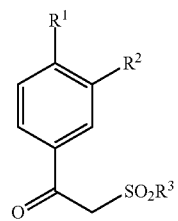

or an isotopologue thereof, via transfer hydrogenation in the presence of a transfer reagent and (1) a metal catalyst and a chiral ligand, or (2) a chiral metal catalyst/ligand complex to form a hydroxylsulfone of Formula (VI):

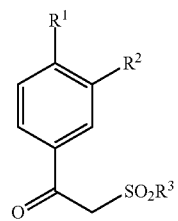

or an isotopologue thereof; and (b) converting the hydroxysulfone of Formula (VI), or an isotopologue thereof, to the aminosulfone of Formula (I), or a salt or isotopologue thereof.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In step (a), the transfer reagent can be any transfer reagent that is capable of promoting transfer hydrogenation. In one embodiment, the transfer reagent is a formate salt. In one embodiment, the transfer reagent is formic acid-triethylamine complex. In one embodiment, the transfer reagents is formic acid or a salt thereof (including, but not limited to, sodium, potassium, and ammonium salt), cyclohexene, cyclohexadiene (including isomers having further substitutients), diimide, hydrazines, or Hantzsch esters. In one embodiment, the transfer reagent is 5:2 formic acid-triethylamine complex. In another embodiment, the transfer reagent is isopropanol.

In step (a), the metal catalyst can be any metal catalyst that is capable of promoting transfer hydrogenation. In one embodiment, the metal catalyst contains a metal such as, but not limited to, copper, nickel, palladium, platinum, rhodium, iridium, and ruthenium. In one embodiment, the metal catalyst contains rhodium. In another embodiment, the metal catalyst contains ruthenium. In yet another embodiment, the metal catalyst contains iridium. In one embodiment, the metal catalyst is Rh(cod)$_2$OTf. In another embodiment, the metal catalyst is Rh(cod)$_2$BF$_4$. In yet another embodiment, the metal catalyst is [Ir(cod)Cl]$_2$. In yet another embodiment, the metal catalyst is Ru(OAc)$_2$. In yet another embodiment, the metal catalyst is RuCl$_2$. In yet another embodiment, the metal catalyst is RuCl(benzene). In yet another embodiment, the metal catalyst is RuCl(p-cymene).

In step (a), the chiral ligand or chiral metal catalyst/ligand complex can be any chiral ligand or chiral metal catalyst/ligand complex that is capable of promoting asymmetric transfer hydrogenation. In one embodiment, the chiral metal catalyst/ligand complex is RuCl(p-cymene)[(S,S)-Ts-DPEN], or a stereoisomer thereof.

In step (a), the transfer hydrogenation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

In step (a), the molar ratio of the chiral ligand to the metal catalyst can be any ratio that is capable of promoting transfer hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

In step (a), the transfer hydrogenation can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is ethanol. In another embodiment, the solvent is 2,2,2-trifluoroethanol. In yet another embodiment, the solvent is acetonitrile.

In step (a), the reaction temperature can be between about 10° C. and about 90° C. In one embodiment, the reaction temperature is between about 20° C. and about 60° C. In one embodiment, the reaction temperature is about 50° C. In another embodiment, the reaction temperature is between about 20° C. and about 25° C.

In step (a), the reaction time can vary from about 1 to about 72 hours, depending on the reaction temperature. In general, the higher the reaction temperature, the shorter is the reaction time. In one embodiment, the reaction time is about 40 hours where the reaction temperature is between about 20° C. and about 25° C.

In one embodiment, the transfer reagent is 5:2 formic acid-triethylamine complex, and the asymmetric transfer hydrogenation of a ketone of Formula (V) occurs in acetonitrile, in the presence of about 1 mol % of RuCl(p-cymene)[(S,S)-Ts-DPEN], at about 20-25° C.

Step (b) is as described above and herein.

In one embodiment, provided is a process for preparing a hydroxysulfone compound of Formula (VI):

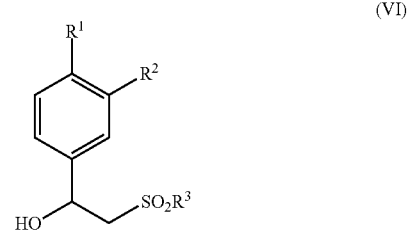

(VI)

or a salt, solvate including a hydrate, isotopologue, or polymorph thereof, wherein R$^1$ and R$^2$ are each independently hydrogen, halogen, substituted or unsubstituted (C$_1$-C$_6$) alkyl, substituted or unsubstituted (C$_1$-C$_6$)alkoxy, (C$_3$-C$_{18}$) cycloalkyl, (C$_3$-C$_6$)cycloalkoxy, cyano, —CF$_3$, or (C$_3$-C$_{18}$) cycloalkyl-(C$_1$-C$_6$)alkoxy, or an isotopologue thereof; and R$^3$ is (C$_1$-C$_6$)alkyl, or an isotopologue thereof;

comprising the steps of (a) reducing a ketone of Formula (V):

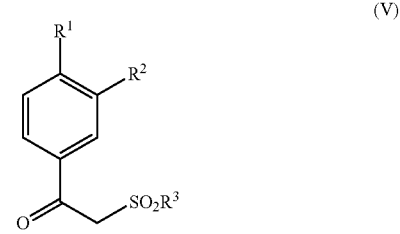

(V)

or an isotopologue thereof, via transfer hydrogenation in the presence of a transfer reagent and (1) a metal catalyst and a chiral ligand, or (2) a chiral metal catalyst/ligand complex to form a hydroxylsulfone of Formula (VI), or an isotopologue thereof.

Step (a) is as described above and herein.

All of the combinations of the above embodiments are encompassed by this invention.

4.2.6 Asymmetric Borane Reduction of a Ketone Substrate

In one embodiment, the processes provided herein utilize asymmetric borane reduction of a ketone substrate, as illustrated in Scheme 7 below.

Scheme 7

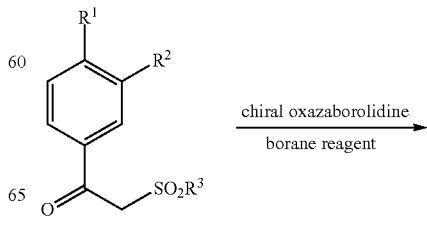

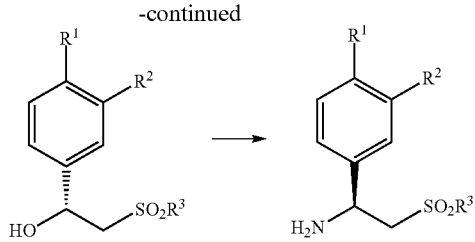

In one embodiment, provided is a process for preparing an aminosulfone compound of Formula (I):

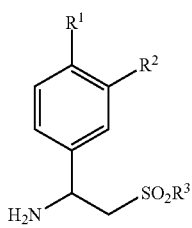

(I)

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$alkoxy, $(C_3-C_{18})$ cycloalkyl, $(C_3-C_6)$cycloalkoxy, cyano, —$CF_3$, or $(C_3-C_{18})$ cycloalkyl-$(C_1-C_6)$alkoxy, or an isotopologue thereof and $R^3$ is $(C_1-C_6)$alkyl, or an isotopologue thereof;
comprising the steps of
(a) reducing a ketone of Formula (V):

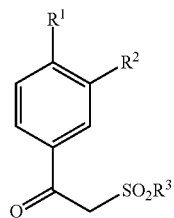

(V)

or an isotopologue thereof, via borane reduction in the presence of a borane reagent and a chiral oxazaborolidine to form a hydroxylsulfone of Formula (VI):

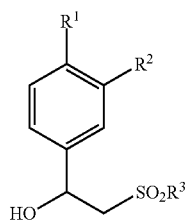

(VI)

or an isotopologue thereof; and
(b) converting the hydroxysulfone of Formula (VI), or an isotopologue thereof, to the aminosulfone of Formula (I), or a salt or isotopologue thereof.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In step (a), the borane reagent can be any borane agent that is capable of promoting borane reduction. In one embodiment, the borane reagent is borane-tetrahydrofuran (THF), borane dimethylsulfide, borane N,N-diethylaniline, diborane, N,N-diisopropylethylamine, or N-ethyl-N-isopropylaniline-borane complex. In one embodiment, the borane reagent is N-ethyl-N-isopropylaniline-borane complex.

Step (a) may occur at any molar ratio of the compound of Formula (V) to the borane reagent. In one embodiment, the molar ratio of the compound of Formula (V) to the borane reagent is from about 10:1 to about 1:10. In one embodiment, the molar ratio of the compound of Formula (V) to the borane reagent is from about 5:1 to about 1:5. In one embodiment, the molar ratio of the compound of Formula (V) to the borane reagent is from about 3:1 to about 1:3. In one embodiment, the molar ratio of the compound of Formula (V) to the borane reagent is from about 1.5:1 to about 1:1.5. In one embodiment, the molar ratio of the compound of Formula (V) to the borane reagent is from about 1:1 to about 1:1.5. In another embodiment, the molar ratio of the compound of Formula (V) to the borane reagent is about 1:1. In one embodiment, the molar ratio of the compound of Formula (V) to the borane reagent is from about 3:1 to about 1:10. In one embodiment, the molar ratio of the compound of Formula (V) to the borane reagent is from about 3:1 to about 1:5.

In step (a), the chiral oxazaborolidine can be any chiral oxazaborolidine that is capable of promoting asymmetric borane reduction. In one embodiment, the chiral oxazaborolidine is CBS-oxazaborolidine. In one embodiment, the chiral oxazaborolidine is a compound of Formula (A):

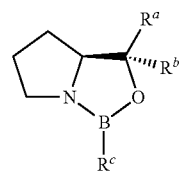

(A)

wherein $R^a$ and $R^b$ are independently substituted or unsubstituted $(C_6-C_{14})$aryl, and $R^c$ is hydrogen, substituted or unsubstituted $(C_1-C_6)$alkyl, or substituted or unsubstituted $(C_6-C_{14})$aryl. In one embodiment, $R^a$ and $R^b$ are independently phenyl or β-naphthyl. In one embodiment, $R^c$ is hydrogen, methyl, n-butyl, or ortho-tolyl. In one embodiment, $R^a$ and $R^b$ are both phenyl, and $R^c$ is methyl.

In step (a), the asymmetric borane reduction can occur with a load of chiral oxazaborolidine no less than about 0.025 mol %. In general, the higher the load of chiral oxazaborolidine, the higher the conversion and the shorter the reaction time. In one embodiment, the load of chiral oxazaborolidine is between about 0.025 mol % and about 20 mol %. In one embodiment, the load of chiral oxazaborolidine is between about 0.025 mol % and about 10 mol %. In one embodiment, the load of chiral oxazaborolidine is between about 0.05 mol % and about 5 mol %. In one embodiment, the load of chiral oxazaborolidine is between about 0.05 mol % and about 2.5 mol %. In one embodiment, the load of chiral oxazaborolidine is between about 0.05 mol % and about 1 mol %. In one embodiment, the load of chiral oxazaborolidine is between about 0.05 mol % and about 0.25 mol %. In one embodiment, the load of chiral oxazaborolidine is about 10 mol %. In another embodiment, the load of chiral oxazaborolidine is about 5 mol %.

In step (a), the asymmetric borane reduction can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is tetrahydrofuran.

In step (a), the reaction temperature can be between about 10° C. and about 90° C. In one embodiment, the reaction temperature is between about 20° C. and about 60° C. In one embodiment, the reaction temperature is about 50° C. In another embodiment, the reaction temperature is about 25° C.

In step (a), the reaction time can vary from about 1 to about 72 hours, depending on the reaction temperature. In general, the higher the reaction temperature, the shorter is the reaction time. In one embodiment, the reaction time is about 24 hours where the reaction temperature is about 25° C.

In one embodiment, the borane reagent is N-ethyl-N-isopropylaniline-borane complex, the molar ratio of the compound of Formula (V) to the borane reagent is about 1:1, and the asymmetric borane reduction of a compound of Formula (V) occurs in tetrahydrofuran, in the presence of about 10 mol % of CBS-oxazaborolidine, at about 25° C.

Step (b) is as described above and herein.

In one embodiment, provided is a process for preparing a hydroxysulfone compound of Formula (VI):

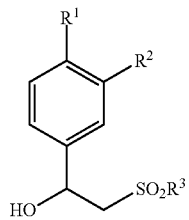

(VI)

or a salt, solvate including a hydrate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, or $(C_3-C_{18})$cycloalkyl-$(C_1-C_6)$alkoxy, or an isotopologue thereof; and $R^3$ is $(C_1-C_6)$alkyl, or an isotopologue thereof;
comprising the steps of
(a) reducing a ketone of Formula (V):

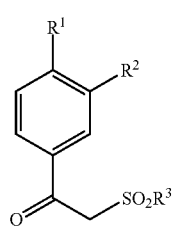

(V)

or an isotopologue thereof, via borane reduction in the presence of a borane reagent and a chiral oxazaborolidine to form a hydroxylsulfone of Formula (VI), or an isotopologue thereof.

Step (a) is as described above and herein.

All of the combinations of the above embodiments are encompassed by this invention.

4.2.7 Polymer-Supported Asymmetric Reduction of a Ketone Substrate

In one embodiment, the processes provided herein utilize polymer-supported asymmetric reduction of a ketone substrate, as illustrated in Scheme 8 below.

Scheme 8

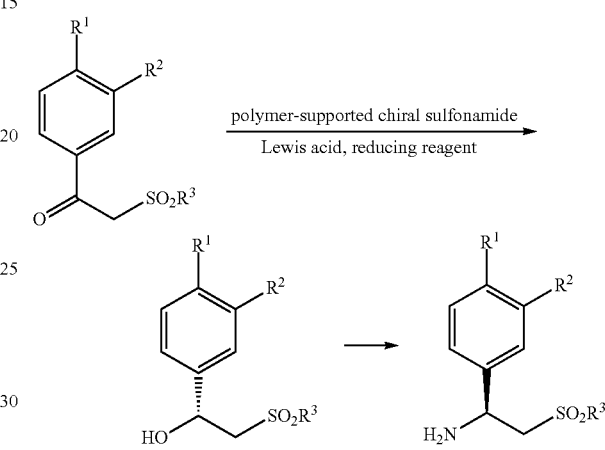

In one embodiment, provided is a process for preparing an aminosulfone compound of Formula (I):

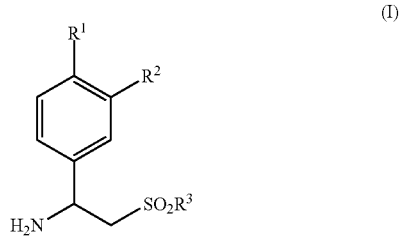

(I)

or a salt, solvate including a hydrate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, or $(C_3-C_{18})$cycloalkyl-$(C_1-C_6)$alkoxy, or an isotopologue thereof; and $R^3$ is $(C_1-C_6)$alkyl, or an isotopologue thereof;
comprising the steps of
(a) reducing a ketone of Formula (V):

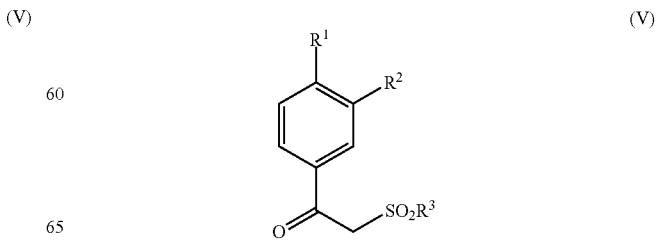

(V)

or an isotopologue thereof, in the presence of a reducing reagent, a Lewis acid, and a polymer-supported chiral sulfonamide to form a hydroxylsulfone of Formula (VI):

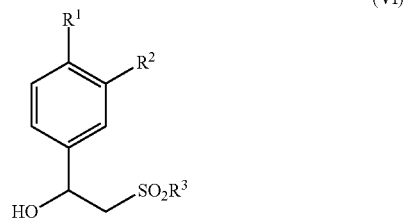

or an isotopologue thereof; and (b) converting the hydroxysulfone of Formula (VI), or an isotopologue thereof, to the aminosulfone of Formula (I), or a salt or isotopologue thereof.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1\text{-}C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In step (a), the reducing reagent can be any reducing reagent that is capable of promoting reduction. In one embodiment, the reducing reagent is $NaBH_4$, or borane dimethylsulfide. In one embodiment, the reducing reagent is $NaBH_4$.

Step (a) may occur at any molar ratio of the compound of Formula (V) to the reducing reagent. In one embodiment, the molar ratio of the compound of Formula (V) to the reducing reagent is from about 10:1 to about 1:10. In one embodiment, the molar ratio of the compound of Formula (V) to the reducing reagent is from about 5:1 to about 1:5. In one embodiment, the molar ratio of the compound of Formula (V) to the reducing reagent is from about 3:1 to about 1:3. In one embodiment, the molar ratio of the compound of Formula (V) to the reducing reagent is from about 1.5:1 to about 1:1.5. In one embodiment, the molar ratio of the compound of Formula (V) to the reducing reagent is from about 1:1 to about 1:1.5. In one embodiment, the molar ratio of the compound of Formula (V) to the reducing reagent is about 1:1.2. In another embodiment, the molar ratio of the compound of Formula (V) to the reducing reagent is about 1:1.

In step (a), the Lewis acid can be any Lewis acid that is capable of promoting reduction. In one embodiment, the Lewis acid is $Me_3SiCl$, or $BF_3 \cdot OEt_2$. In one embodiment, the Lewis acid is $Me_3SiCl$.

Step (a) may occur at any molar ratio of the compound of Formula (V) to the Lewis acid. In one embodiment, the molar ratio of the compound of Formula (V) to the Lewis acid is from about 10:1 to about 1:10. In one embodiment, the molar ratio of the compound of Formula (V) to the Lewis acid is from about 5:1 to about 1:5. In one embodiment, the molar ratio of the compound of Formula (V) to the Lewis acid is from about 3:1 to about 1:3. In one embodiment, the molar ratio of the compound of Formula (V) to the Lewis acid is from about 1.5:1 to about 1:1.5. In one embodiment, the molar ratio of the compound of Formula (V) to the Lewis acid is from about 1:1 to about 1:1.5. In one embodiment, the molar ratio of the compound of Formula (V) to the Lewis acid is about 1:1.2. In another embodiment, the molar ratio of the compound of Formula (V) to the Lewis acid is about 1:1.

In step (a), the polymer-supported chiral sulfonamide can be any polymer-supported chiral sulfonamide that is capable of promoting asymmetric reduction. In one embodiment, the polymer-supported chiral sulfonamide is a compound of the following formula:

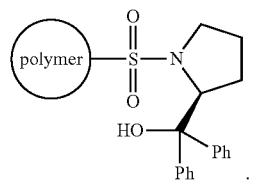 [SMILES: CS(=O)(=O)N1CCC[C@H]1C(O)(c1ccccc1)c1ccccc1]

In step (a), the asymmetric reduction can occur with a load of polymer-supported chiral sulfonamide no less than about 0.025 mol %. In general, the higher the load of polymer-supported chiral sulfonamide, the higher the conversion and the shorter the reaction time. In one embodiment, the load of polymer-supported chiral sulfonamide is between about 0.025 mol % and about 100 mol %. In one embodiment, the load of polymer-supported chiral sulfonamide is between about 0.25 mol % and about 75 mol %. In one embodiment, the load of polymer-supported chiral sulfonamide is between about 1 mol % and about 50 mol %. In one embodiment, the load of polymer-supported chiral sulfonamide is between about 5 mol % and about 40 mol %. In one embodiment, the load of polymer-supported chiral sulfonamide is between about 10 mol % and about 30 mol %. In one embodiment, the load of polymer-supported chiral sulfonamide is between about 15 mol % and about 25 mol %. In one embodiment, the load of polymer-supported chiral sulfonamide is about 25 mol %. In another embodiment, the load of polymer-supported chiral sulfonamide is about 10 mol %.

In step (a), the asymmetric reduction can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is tetrahydrofuran.

In step (a), the reaction temperature can be between about 10° C. and about 90° C. In one embodiment, the reaction temperature is between about 20° C. and about 60° C. In one embodiment, the reaction temperature is about 50° C. In another embodiment, the reaction temperature is about 25° C. In another embodiment, the reaction temperature is about 70° C. In another embodiment, the reaction temperature is about refluxing temperature of tetrahydrofuran.

In step (a), the reaction time can vary from about 1 to about 72 hours, depending on the reaction temperature. In general, the higher the reaction temperature, the shorter is the reaction time. In one embodiment, the reaction time is about 24 hours where the reaction temperature is about 25° C. In one embodiment, the reaction time is about 3 hours.

In one embodiment, the reducing reagent is $NaBH_4$, the Lewis acid is $Me_3SiCl$, and the asymmetric reduction of a compound of Formula (V) occurs in in the presence of about 25 mol % of a polymer-supported chiral sulfonamide of the following Formula:

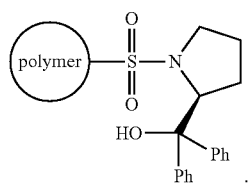

Step (b) is as described above and herein.

In one embodiment, provided is a process for preparing a hydroxysulfone compound of Formula (VI):

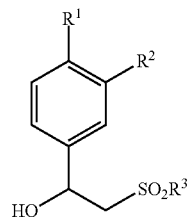

(VI)

or a salt, solvate including a hydrate, isotopologue, or polymorph thereof, wherein $R^1$ and $R^2$ are each independently hydrogen, halogen, substituted or unsubstituted ($C_1$-$C_6$) alkyl, substituted or unsubstituted ($C_1$-$C_6$)alkoxy, ($C_3$-$C_{18}$) cycloalkyl, ($C_3$-$C_6$)cycloalkoxy, cyano, —$CF_3$, or ($C_3$-$C_{18}$) cycloalkyl-($C_1$-$C_6$)alkoxy, or an isotopologue thereof; and $R^3$ is ($C_1$-$C_6$)alkyl, or an isotopologue thereof;

comprising the steps of (a) reducing a ketone of Formula (V):

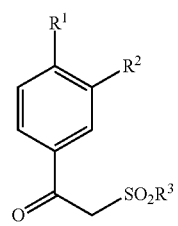

(V)

or an isotopologue thereof, in the presence of a reducing reagent and a polymer-supported chiral sulfonamide to form a hydroxylsulfone of Formula (VI), or an isotopologue thereof.

Step (a) is as described above and herein.

All of the combinations of the above embodiments are encompassed by this invention.

4.2.8 Yeast or Fungus-Mediated Asymmetric Reduction of a Ketone Substrate

In one embodiment, the processes provided herein utilize yeast or fungus-mediated asymmetric reduction of a ketone substrate, as illustrated in Scheme 9 below.

Scheme 9

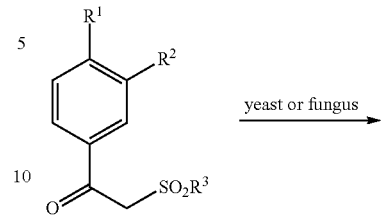

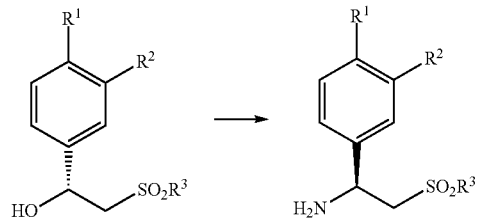

In one embodiment, provided is a process for preparing an aminosulfone compound of Formula (I):

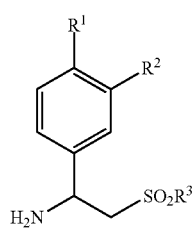

(I)

or a salt, solvate including a hydrate, isotopologue, or polymorph thereof, wherein $R^1$ and $R^2$ are each independently hydrogen, halogen, substituted or unsubstituted ($C_1$-$C_6$) alkyl, substituted or unsubstituted ($C_1$-$C_6$)alkoxy, ($C_3$-$C_{18}$) cycloalkyl, ($C_3$-$C_6$)cycloalkoxy, cyano, —$CF_3$, or ($C_3$-$C_{18}$) cycloalkyl-($C_1$-$C_6$)alkoxy, or an isotopologue thereof and $R^3$ is ($C_1$-$C_6$)alkyl, or an isotopologue thereof;

comprising the steps of (a) reducing a ketone of Formula (V):

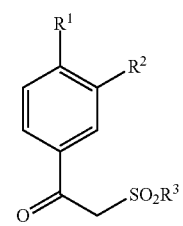

(V)

or an isotopologue thereof, via yeast or fungus-mediated asymmetric reduction in the presence of a yeast or fungus to form a hydroxylsulfone of Formula (VI):

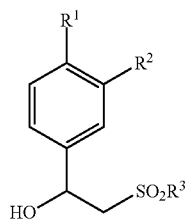

(VI)

or an isotopologue thereof; and
(b) converting the hydroxysulfone of Formula (VI), or an isotopologue thereof, to the aminosulfone of Formula (I), or a salt or isotopologue thereof.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In step (a), the yeast or fungus can be any yeast or fungus that is capable of promoting yeast or fungus-mediated asymmetric reduction. In one embodiment, step (a) occurs in the presence of a yeast. In one embodiment, the yeast is Baker's yeast. In one embodiment, step (a) occurs in the presence of a fungus. In one embodiment, the fungus is *Pichia farinose* IAM 4682, *Rhodococcus rhodochrous*, or *Curvularia lunata*. In one embodiment, the fungus is *Curvularia lunata*.

Step (b) is as described above and herein.

In one embodiment, provided is a process for preparing a hydroxysulfone compound of Formula (VI):

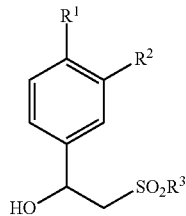

(VI)

or a salt, solvate including a hydrate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, or $(C_3-C_{18})$cycloalkyl-$(C_1-C_6)$alkoxy, or an isotopologue thereof; and $R^3$ is $(C_1-C_6)$alkyl, or an isotopologue thereof;
comprising the steps of
(a) reducing a ketone of Formula (V):

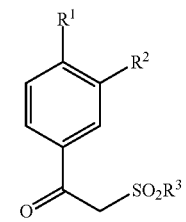

(V)

or an isotopologue thereof, via yeast or fungus-mediated asymmetric reduction in the presence of a yeast or fungus to form a hydroxylsulfone of Formula (VI), or an isotopologue thereof.

Step (a) is as described above and herein.

All of the combinations of the above embodiments are encompassed by this invention.

4.2.9 Asymmetric Hydrosilylation of a Ketone Substrate

In one embodiment, the processes provided herein utilize asymmetric hydrosilylation of a ketone substrate, as illustrated in Scheme 10 below.

Scheme 10

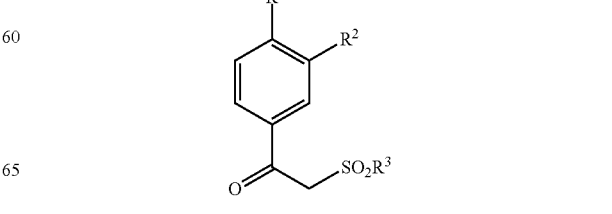

In one embodiment, provided is a process for preparing an aminosulfone compound of Formula (I):

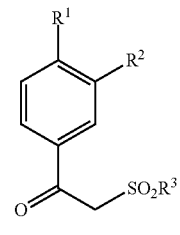

(I)

or a salt, solvate including a hydrate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, or $(C_3-C_{18})$cycloalkyl-$(C_1-C_6)$alkoxy, or an isotopologue thereof; and $R^3$ is $(C_1-C_6)$alkyl, or an isotopologue thereof;
comprising the steps of
(a) reducing a ketone of Formula (V):

(V)

or an isotopologue thereof, via hydrosilylation in the presence of a silane and (1) a metal catalyst and a chiral ligand, or (2) a chiral metal catalyst/ligand complex to form a hydroxylsulfone of Formula (VI):

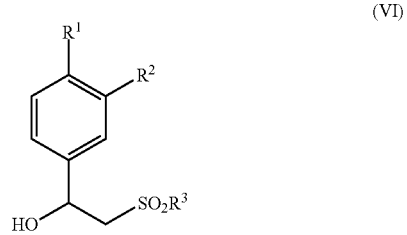

(VI)

or an isotopologue thereof; and
(b) converting the hydroxysulfone of Formula (VI), or an isotopologue thereof, to the aminosulfone of Formula (I), or a salt or isotopologue thereof.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof; and $R^3$ is Me, or an isotopologue thereof.

In step (a), the silane can be any silane that is capable of promoting hydrosilylation. In one embodiment, the silane is polymethylhydrosilane, or diphenylsilane.

Step (a) may occur at any molar ratio of the compound of Formula (V) to the silane. In one embodiment, the molar ratio of the compound of Formula (V) to the silane is from about 10:1 to about 1:10. In one embodiment, the molar ratio of the compound of Formula (V) to the silane is from about 5:1 to about 1:5. In one embodiment, the molar ratio of the compound of Formula (V) to the silane is from about 3:1 to about 1:3. In one embodiment, the molar ratio of the compound of Formula (V) to the silane is from about 1.5:1 to about 1:1.5. In one embodiment, the molar ratio of the compound of Formula (V) to the silane is from about 1:1 to about 1:1.5. In one embodiment, the molar ratio of the compound of Formula (V) to the silane is about 1:1.1. In another embodiment, the molar ratio of the compound of Formula (V) to the silane is about 1:1.

In step (a), the metal catalyst can be any metal catalyst that is capable of promoting hydrosilylation. In one embodiment, the metal catalyst contains a metal such as, but not limited to, zinc, copper, nickel, palladium, platinum, rhodium, iridium, and ruthenium. In one embodiment, the metal catalyst contains rhodium. In another embodiment, the metal catalyst contains zinc. In yet another embodiment, the metal catalyst contains copper. In one embodiment, the metal catalyst is CuCl, Cu(OAc)$_2$, or [Rh(cod)Cl]$_2$.

In step (a), the chiral ligand or chiral metal catalyst/ligand complex can be any chiral ligand or chiral metal catalyst/ligand complex that is capable of promoting asymmetric hydrosilylation. In one embodiment, the chiral ligand is DTBM-Segphos, Xyl-Meo-Biphep, or 2-(2-oxazolin-2-ylmethyl)pyridine.

In step (a), the hydrosilylation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

In step (a), the molar ratio of the chiral ligand to the metal catalyst can be any ratio that is capable of promoting transfer hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

Step (b) is as described above and herein.

In one embodiment, provided is a process for preparing a hydroxysulfone compound of Formula (VI):

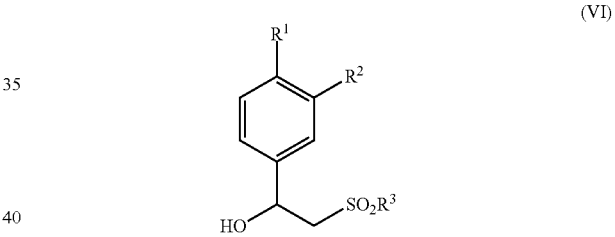

(VI)

or a salt, solvate including a hydrate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —CF$_3$, or $(C_3-C_{18})$cycloalkyl-$(C_1-C_6)$alkoxy, or an isotopologue thereof; and $R^3$ is $(C_1-C_6)$alkyl, or an isotopologue thereof;
comprising the steps of
(a) reducing a ketone of Formula (V):

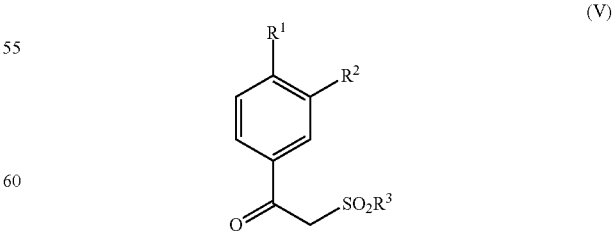

(V)

or an isotopologue thereof, via hydrosilylation in the presence of a silane and (1) a metal catalyst and a chiral ligand, or (2) a chiral metal catalyst/ligand complex to form a hydroxylsulfone of Formula (VI), or an isotopologue thereof.

Step (a) is as described above and herein.

All of the combinations of the above embodiments are encompassed by this invention.

4.2.10 Kinetic Resolution

In one embodiment, the processes provided herein utilize kinetic resolution of a hydroxysulfone substrate, as illustrated in Scheme 11 below.

Scheme 11

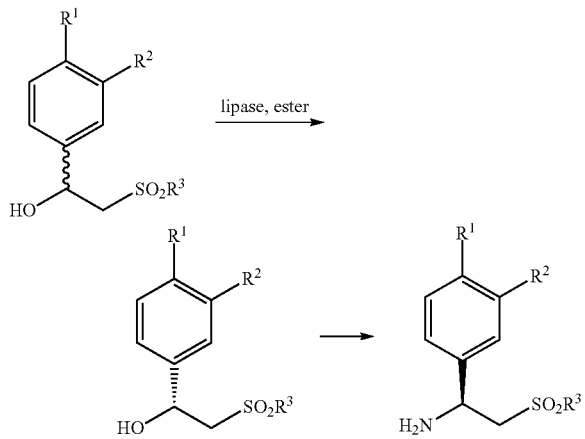

In one embodiment, provided is a process for preparing an aminosulfone compound of Formula (I):

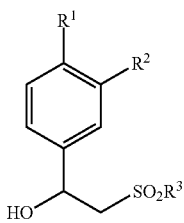
(I)

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$alkoxy, $(C_3-C_{18})$ cycloalkyl, $(C_3-C_6)$cycloalkoxy, cyano, —$CF_3$, or $(C_3-C_{18})$ cycloalkyl-$(C_1-C_6)$alkoxy, or an isotopologue thereof and $R^3$ is $(C_1-C_6)$alkyl, or an isotopologue thereof;

comprising the steps of (a) contacting a hydroxysulfone of Formula (VI):

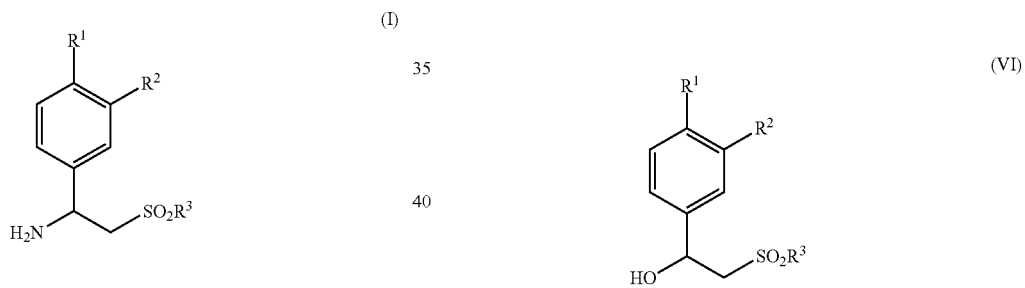
(VI)

or an isotopologue thereof, with a lipase and an ester to form an enantiomerically enriched hydroxylsulfone of Formula (VI), or an isotopologue thereof and (b) converting the enantiomerically enriched hydroxysulfone of Formula (VI), or an isotopologue thereof, to the aminosulfone of Formula (I), or a salt or isotopologue thereof.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof and $R^3$ is Me, or an isotopologue thereof.

In step (a), the lipase can be any lipase that is capable of promoting kinetic resolution reduction. In one embodiment, the lipase is porcine pancreatic lipase.

In step (a), the ester can be any ester that is capable of promoting kinetic resolution reaction. In one embodiment, the ester is $(C_{1-6}$ alkyl$)$-COO—$(C_{1-6}$ alkyl$)$, wherein each $C_{1-6}$ alkyl is independently and optionally substituted with one or more halogen. In one embodiment, the ester is $BuCO_2CH_2CCl_3$.

Step (b) is as described above and herein.

In one embodiment, provided is a process for preparing a hydroxysulfone compound of Formula (VI):

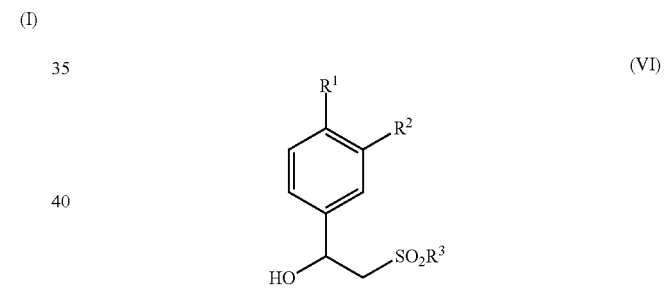
(VI)

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$alkoxy, $(C_3-C_{18})$ cycloalkyl, $(C_3-C_6)$cycloalkoxy, cyano, —$CF_3$, or $(C_3-C_{18})$ cycloalkyl-$(C_1-C_6)$alkoxy, or an isotopologue thereof; and $R^3$ is $(C_1-C_6)$alkyl, or an isotopologue thereof;

comprising the steps of (a) contacting a hydroxysulfone of Formula (VI), or an isotopologue thereof, with a lipase and an ester to form an enantiomerically enriched hydroxylsulfone of Formula (VI), or an isotopologue thereof.

Step (a) is as described above and herein.

All of the combinations of the above embodiments are encompassed by this invention.

4.2.11 Asymmetric Hydrogenation of an N-Acyl Hydrazone Substrate

In one embodiment, the processes provided herein utilize asymmetric hydrogenation of an N-acyl hydrazone substrate, as illustrated in Scheme 12 below.

Scheme 12

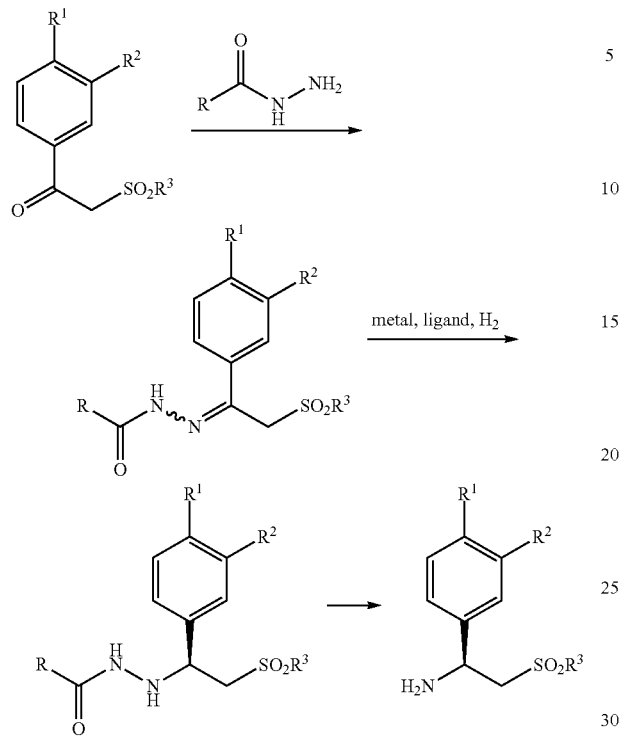

In one embodiment, provided is a process for preparing an aminosulfone compound of Formula (I):

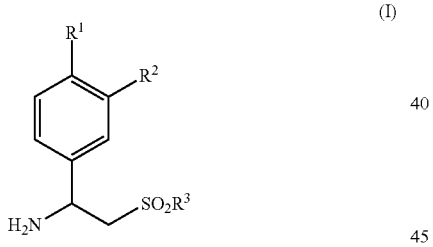

(I)

or a salt, solvate including a hydrate, isotopologue, or polymorph thereof, wherein $R^1$ and $R^2$ are each independently hydrogen, halogen, substituted or unsubstituted ($C_1$-$C_6$) alkyl, substituted or unsubstituted ($C_1$-$C_6$)alkoxy, ($C_3$-$C_{18}$) cycloalkyl, ($C_3$-$C_6$)cycloalkoxy, cyano, —$CF_3$, or ($C_3$-$C_{18}$) cycloalkyl-($C_1$-$C_6$)alkoxy, or an isotopologue thereof; and $R^3$ is ($C_1$-$C_6$)alkyl, or an isotopologue thereof;
comprising the steps of
(a) reacting a ketone of Formula (V):

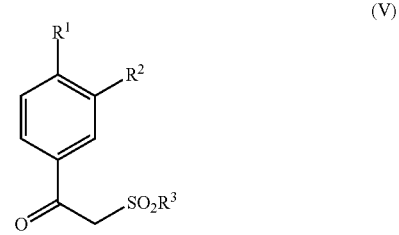

(V)

or an isotopologue thereof, with an N-acyl hydrazine to form a compound of Formula (VII):

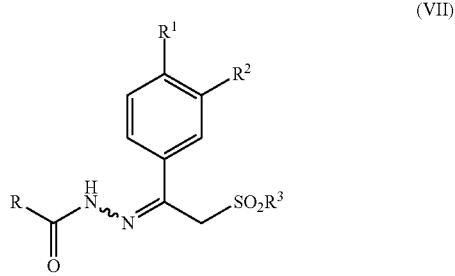

(VII)

or an isotopologue thereof, wherein R is hydrogen; ($C_1$-$C_6$) alkyl, itself optionally substituted with one or more halogen; or 5 to 10 membered aryl or heteroaryl, optionally substituted with one or more halogen; or an isotopologue thereof;

(b) reducing the compound of Formula (VII), or an isotopologue thereof, via hydrogenation in the presence of (1) a metal catalyst and a chiral ligand, or (2) a chiral metal catalyst/ligand complex to form a compound of Formula (VIII):

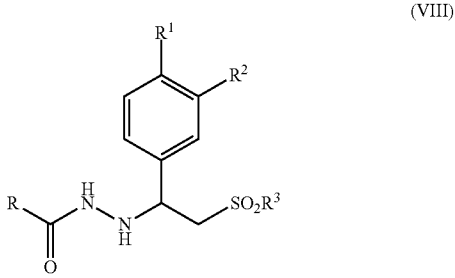

(VIII)

or an isotopologue thereof; and (c) converting the compound of Formula (VIII), or an isotopologue thereof, to the aminosulfone of Formula (I), or a salt or isotopologue thereof.

In one embodiment, the hydrogenation is conducted with hydrogen gas.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted ($C_1$-$C_6$)alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof and $R^3$ is Me, or an isotopologue thereof.

In one embodiment, R is 5 to 10 membered aryl or heteroaryl, itself optionally substituted with one or more halogen. In one embodiment, R is phenyl.

All of the combinations of the above embodiments are encompassed by this invention.

4.2.12 Asymmetric Borane Reduction of an Enamine Substrate

In one embodiment, the processes provided herein utilize asymmetric borane reduction of an enamine substrate, as illustrated in Scheme 13 below.

Scheme 13

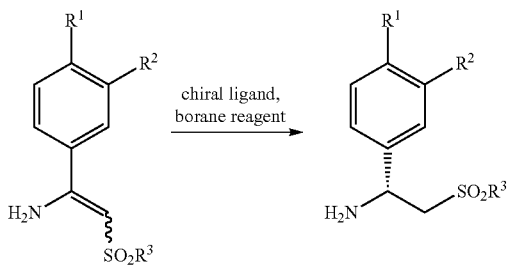

In one embodiment, provided is a process for preparing an aminosulfone compound of Formula (I):

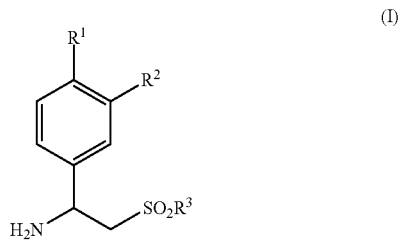

or a salt, solvate including a hydrate, isotopologue, or polymorph thereof, wherein $R^1$ and $R^2$ are each independently hydrogen, halogen, substituted or unsubstituted $(C_1-C_6)$ alkyl, substituted or unsubstituted $(C_1-C_6)$alkoxy, $(C_3-C_{18})$ cycloalkyl, $(C_3-C_6)$cycloalkoxy, cyano, —$CF_3$, or $(C_3-C_{18})$ cycloalkyl-$(C_1-C_6)$alkoxy, or an isotopologue thereof and $R^3$ is $(C_1-C_6)$alkyl, or an isotopologue thereof.
comprising the step of reducing an enamine of Formula (II):

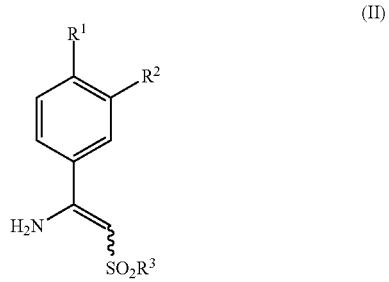

or a salt or isotopologue thereof, via borane reduction in the presence of a borane reagent and a chiral ligand.

In one embodiment, provided herein are processes described above for preparing an aminosulfone compound of Formula (I), or a salt, solvate including a hydrate, isotopologue, or polymorph thereof, wherein $R^1$ and $R^2$ are substituted or unsubstituted $(C_1-C_6)$alkoxy, or an isotopologue thereof. In one embodiment, provided herein are processes described above for preparing an aminosulfone compound of Formula (I), or a salt, solvate including a hydrate, isotopologue, or polymorph thereof, wherein $R^1$ is OMe, or an isotopologue thereof; $R^2$ is OEt, or an isotopologue thereof and $R^3$ is Me, or an isotopologue thereof.

The borane reagent can be any borane agent that is capable of promoting borane reduction. In one embodiment, the borane reagent is borane-tetrahydrofuran (THF), borane dimethylsulfide, borane N,N-diethylaniline, diborane, N,N-diisopropylethylamine, or N-ethyl-N-isopropylaniline-borane complex. In one embodiment, the borane reagent is borane N,N-diethylaniline.

The borane reduction may occur at any molar ratio of the compound of Formula (II) to the borane reagent. In one embodiment, the molar ratio of the compound of Formula (II) to the borane reagent is from about 10:1 to about 1:10. In one embodiment, the molar ratio of the compound of Formula (II) to the borane reagent is from about 5:1 to about 1:5. In one embodiment, the molar ratio of the compound of Formula (II) to the borane reagent is from about 3:1 to about 1:3. In one embodiment, the molar ratio of the compound of Formula (II) to the borane reagent is from about 1.5:1 to about 1:1.5. In one embodiment, the molar ratio of the compound of Formula (II) to the borane reagent is from about 1:1 to about 1:1.5. In another embodiment, the molar ratio of the compound of Formula (II) to the borane reagent is about 1:1. In yet another embodiment, the molar ratio of the compound of Formula (II) to the borane reagent is about 1:1.8. In one embodiment, the molar ratio of the compound of Formula (II) to the borane reagent is from about 3:1 to about 1:10. In one embodiment, the molar ratio of the compound of Formula (V) to the borane reagent is from about 3:1 to about 1:5.

The chiral ligand can be any chiral ligand that is capable of promoting asymmetric borane reduction. In one embodiment, the chiral ligand is (1R,2S)-aminoindanol, or a stereoisomer thereof. In one embodiment, the chiral ligand is (1R,2S)-aminoindanol.

The borane reduction may occur at any molar ratio of the compound of Formula (II) to the chiral ligand. In one embodiment, the molar ratio of the compound of Formula (II) to the chiral ligand is from about 10:1 to about 1:10. In one embodiment, the molar ratio of the compound of Formula (II) to the chiral ligand is from about 5:1 to about 1:5. In one embodiment, the molar ratio of the compound of Formula (II) to the chiral ligand is from about 3:1 to about 1:3. In one embodiment, the molar ratio of the compound of Formula (II) to the chiral ligand is from about 1.5:1 to about 1:1.5. In one embodiment, the molar ratio of the compound of Formula (II) to the chiral ligand is from about 1:1 to about 1:1.5. In another embodiment, the molar ratio of the compound of Formula (II) to the chiral ligand is about 1:1.

The borane reduction can occur in a solvent such as, but not limited to, ethyl acetate, diethyl ether, tetrahydrofuran, 1,4-dioxane, acetonitrile, dichloromethane, chloroform, N-methylpyrrolidinone, dimethyl formamide, dimethyl sulfoxide, formic acid, acetic acid, methanol, ethanol, isopropanol, 2,2,2-trifluoroethanol, and mixtures thereof. In one embodiment, the solvent is tetrahydrofuran.

The reaction temperature can be between about −50° C. and about 90° C. In one embodiment, the reaction temperature is between about −50° C. and about 60° C. In one embodiment, the reaction temperature is about −3° C.

In step (a), the reaction time can vary from about 1 to about 120 hours, depending on the reaction temperature. In general, the higher the reaction temperature, the shorter is the reaction time. In one embodiment, the reaction time is about 72 hours where the reaction temperature is about −3° C.

In one embodiment, the borane reagent is borane N,N-diethylaniline, the molar ratio of the compound of Formula (II) to the borane reagent is about 1:1.8, the chiral ligand is (1R,2S)-aminoindanol, the molar ratio of the compound of Formula (II) to the chiral ligand is about 1:1, and the asymmetric borane reduction of a compound of Formula (II) occurs in tetrahydrofuran.

All of the combinations of the above embodiments are encompassed by this invention.

4.2.13 Preparation of the Starting Materials

The starting materials (e.g., an enamine of Formula (II) and a ketone of Formula (V)) for all of the synthetic processes provided herein can be prepared using methods known in the art or provided herein.

In one embodiment, an enamine of Formula (II) can be prepared by reacting the corresponding benzonitrile with LiCH$_2$SO$_2$R$^3$, as illustrated in Scheme 14 below.

Scheme 14

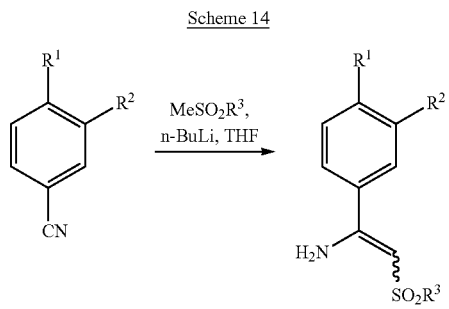

In one embodiment, the enamine of Formula (II), as used in all of the synthetic processes provided herein, has greater than about 80%, about 85%, about 90%, about 95%, about 98%, about 99.0%, about 99.5%, or about 99.9% purity. In another embodiment, the enamine of Formula (II), as used in all of the synthetic processes provided herein, has greater than about 50%, but less than about 80%, about 85%, about 90%, about 95%, about 98%, about 99.0%, about 99.5%, or about 99.9% purity.

In one embodiment, the enamine of Formula (II), as used in all of the synthetic processes provided herein, contains certain amount of the amine of Formula (I). In one embodiment, the enamine of Formula (II), as used in all of the synthetic processes provided herein, contains less than about 20%, less than about 15%, less than about 10%, less than about 5%, less than about 3%, less than about 2%, less than about 1%, less than about 0.5%, or less than about 0.1% of the amine of Formula (I).

All of the combinations of the above embodiments are encompassed by this invention.

5. EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); M (molar); mM (millimolar); μM (micromolar); eq. (equivalent); mmol (millimoles); Hz (Hertz); MHz (megahertz); hr or hrs (hour or hours); min (minutes); and MS (mass spectrometry).

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Example 1

Synthesis of 1-(3-ethoxy-4-methoxyphenyl)-2-(methylsulfonyl)ethenamine

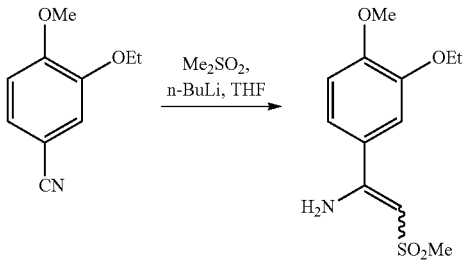 [SMILES: CCOc1cc(C#N)ccc1OC ; CCOc1cc(C(N)=CS(C)(=O)=O)ccc1OC]

A slurry of dimethylsulfone (85 g, 903 mmol) in THF (480 ml) was treated with a 1.6M solution of n-butyllithium in hexane (505 ml, 808 mmol) at 0-5° C. The resulting mixture was agitated for 1 hour then a solution of 3-ethoxy-4-methoxybenzonitrile (80 g, 451 mmol) in THF (240 ml) was added at 0-5° C. The mixture was agitated at 0-5° C. for 0.5 hour, warmed to 25-30° C. over 0.5 hour and then agitated for 1 hour. Water (1.4 L) was added at 25-30° C. and the reaction mass was agitated overnight at room temperature (20-30° C.). The solid was filtered and subsequently washed with a 2:1 mixture of water:THF (200 ml), water (200 ml) and heptane (2×200 ml). The solid was dried under reduced pressure at 40-45° C. to provide the product as a white solid (102 g, 83% yield); $^1$H NMR (DMSO-d$_6$) δ 1.34 (t, J=7.0 Hz, 3H), 2.99 (s, 3H), 3.80 (s, 3H), 4.08 (q, J=7.0 Hz, 2H), 5.03 (s, 1H), 6.82 (s, 2H), 7.01 (d, J=8.5 Hz, 1H), 7.09-7.22 (m, 2H).

Example 2

Synthesis of (R)-1-(3-ethoxy-4-methoxyphenyl)-2-(methylsulfonyl)ethanamine

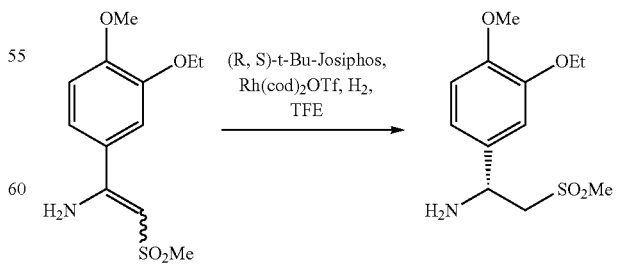

A solution of bis(1,5-cyclooctadiene)rhodium(I) trifluoromethanesulfonate (36 mg, 0.074 mmol) and (R)-1-[(S)-2-(diphenylphosphino)ferrocenyl]ethyldi-tert-butylphosphine (40 mg, 0.074 mmol) in 25 mL of 2,2,2-trifluoroethanol was prepared under nitrogen. To this solution was then charged 1-(3-ethoxy-4-methoxyphenyl)-2-(methylsulfonyl)ethenamine (2.0 g, 7.4 mmol). The resulting mixture was heated to 50° C. and hydrogenated under 90 psig hydrogen pressure. After 18 h, the mixture was cooled to ambient temperature and removed from the hydrogenator. The mixture was evaporated and the residue was purified by chromatography on a C18 reverse phase column using a water-acetonitrile gradient. The appropriate fractions were pooled and evaporated to ~150 mL. To this solution was added brine (20 mL), and the resulting solution was extracted with EtOAc (3×50 mL). The combined organic layers were dried (MgSO$_4$) and evaporated to provide the product as a white crystalline solid (1.4 g, 70% yield); achiral HPLC (Hypersil BDS C$_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 9.11 (99.6%); chiral HPLC (Chiralpak AD-H 5.0 μm Daicel, 250×4.6 mm, 1.0 mL/min, 280 nm, 70:30:0.1 heptane-i-PrOH-diethylamine): 7.32 (97.5%), 8.26 (2.47%); $^1$H NMR (DMSO-d$_6$) δ 1.32 (t, J=7.0 Hz, 3H), 2.08 (s, 2H), 2.96 (s, 3H), 3.23 (dd, J=3.6, 14.4 Hz, 1H), 3.41 (dd, J=9.4, 14.4 Hz, 1H), 3.73 (s, 3H), 4.02 (q, J=7.0 Hz, 2H), 4.26 (dd, J=3.7, 9.3 Hz, 1H), 6.89 (s, 2H), 7.02 (s, 1H); $^{13}$C NMR (DMSO-d$_6$) δ 14.77, 41.98, 50.89, 55.54, 62.03, 63.68, 111.48, 111.77, 118.36, 137.30, 147.93, 148.09.

Example 3

Synthesis of (S)-1-(3-ethoxy-4-methoxyphenyl)-2-(methylsulfonyl)ethanamine N—Ac-L-Leu salt

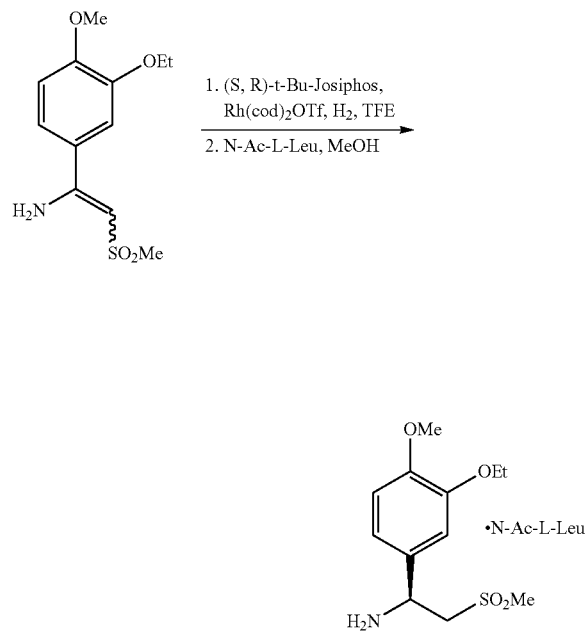

A solution of bis(1,5-cyclooctadiene)rhodium(I) trifluoromethanesulfonate (17 mg, 0.037 mmol) and (S)-1-[(R)-2-(diphenylphosphino)ferrocenyl]ethyldi-tert-butylphosphine (20 mg, 0.037 mmol) in 10 mL of 2,2,2-trifluoroethanol was prepared under nitrogen. To this solution was then charged 1-(3-ethoxy-4-methoxyphenyl)-2-(methylsulfonyl)ethenamine (2.0 g, 7.4 mmol). The resulting mixture was heated to 50° C. and hydrogenated under 90 psig hydrogen pressure. After 18 h, the mixture was cooled to ambient temperature and removed from the hydrogenator. Ecosorb C-941 (200 mg) was added and the mixture was stirred at ambient temperature for 3 h. The mixture was filtered through Celite, and the filter was washed with additional trifluoroethanol (2 mL). Then, the mixture was heated to 55° C., and a solution of N-acetyl-L-leucine (1.3 g, 7.5 mmol) was added dropwise over the course of 1 h. Stirring proceeded at the same temperature for 1 h following completion of the addition, and then the mixture was cooled to 22° C. over 2 h and stirred at this temperature for 16 h. The crystalline product was filtered, rinsed with methanol (2×5 mL), and dried under vacuum at 45° C. to provide the product as a white solid (2.6 g, 80% yield); achiral HPLC (Hypersil BDS C$_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 8.57 (99.8%); chiral HPLC (Chiralpak AD-H 5.0 μm Daicel, 250×4.6 mm, 1.0 mL/min, 280 nm, 70:30:0.1 heptane-i-PrOH-diethylamine): 8.35 (99.6%); $^1$H NMR (DMSO-d$_6$) δ 0.84 (d, 3H), 0.89 (d, J=6.6 Hz, 3H), 1.33 (t, J=7.0 Hz, 3H), 1.41-1.52 (m, 2H), 1.62 (dt, J=6.7, 13.5 Hz, 1H), 1.83 (s, 3H), 2.94 (s, 3H), 3.28 (dd, J=4.0, 14.4 Hz, 1H), 3.44 (dd, J=9.1, 14.4 Hz, 1H), 3.73 (s, 3H), 4.02 (q, J=6.9 Hz, 2H), 4.18 (q, J=7.7 Hz, 1H), 4.29 (dd, J=4.0, 9.1 Hz, 1H), 5.46 (br, 3H), 6.90 (s, 2H), 7.04 (s, 1H), 8.04 (d, J=7.9 Hz, 1H); Anal. (C$_{20}$H$_{34}$N$_2$O$_7$S) C, H, N. Calcd C, 53.79; H, 7.67; N, 6.27. Found C, 53.78; H, 7.57; N, 6.18.

Example 4

Selected Ligands for Asymmetric Hydrogenation of Enamine

For each reaction, a mixture of bis(1,5-cyclooctadiene)rhodium(I) trifluoromethanesulfonate (9 mg, 0.018 mmol), 2,2,2-trifluoroethanol (3 mL), and the appropriate ligand (0.037 mmol) or a preformed complex of the ligand and metal (0.018 mmol) was prepared under nitrogen. Then, 1-(3-ethoxy-4-methoxyphenyl)-2-(methylsulfonyl)ethenamine (100 mg, 0.37 mmol) was added. The resultant mixture was heated to 50° C. and hydrogenated under 250 psig hydrogen pressure. After 18 h, the mixture was removed from the hydrogenator and monitored by achiral HPLC (Hypersil BDS C$_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min). Reactions containing >10 Area % of the product enamine were also assayed for chiral purity by chiral HPLC (Chiralpak AD-H 5.0 μm Daicel, 250×4.6 mm, 1.0 mL/min, 280 nm, 70:30:0.1 heptane-1-PrOH-diethylamine or 50:40:10:0.1 heptane-EtOH-i-PrOH-diethylamine). The results are listed in Table 1 below.

TABLE 1

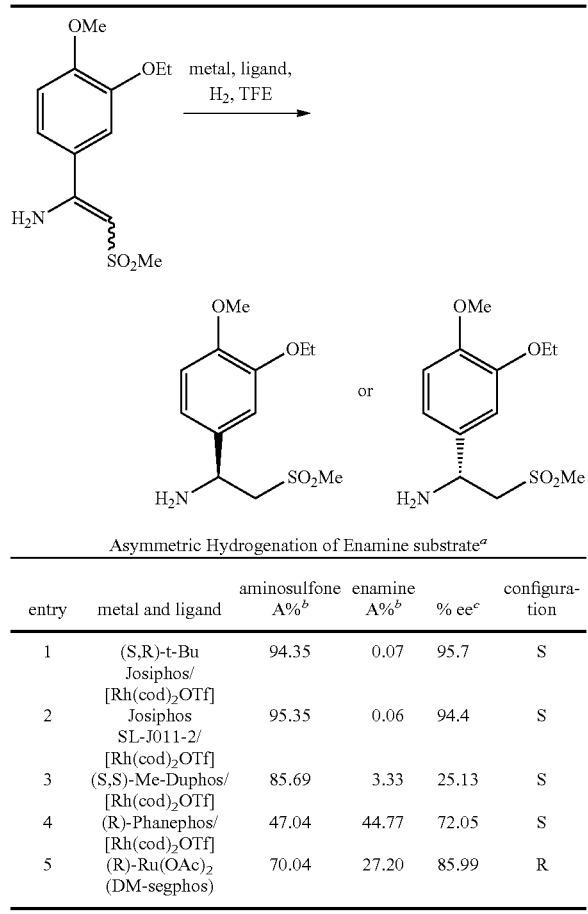

Asymmetric Hydrogenation of Enamine substrate[a]

| entry | metal and ligand | aminosulfone A%[b] | enamine A%[b] | % ee[c] | configuration |
|---|---|---|---|---|---|
| 1 | (S,R)-t-Bu Josiphos/ [Rh(cod)₂OTf] | 94.35 | 0.07 | 95.7 | S |
| 2 | Josiphos SL-J011-2/ [Rh(cod)₂OTf] | 95.35 | 0.06 | 94.4 | S |
| 3 | (S,S)-Me-Duphos/ [Rh(cod)₂OTf] | 85.69 | 3.33 | 25.13 | S |
| 4 | (R)-Phanephos/ [Rh(cod)₂OTf] | 47.04 | 44.77 | 72.05 | S |
| 5 | (R)-Ru(OAc)₂ (DM-segphos) | 70.04 | 27.20 | 85.99 | R |

[a]Reaction conditions: in 30 Vol. 2,2,2-trifluoroethanol (TFE), S/C = 20, 2:1 ligand/metal, 50° C., 250 psig hydrogen pressure 18 h.
[b]Area % observed in achiral HPLC with detector set to 278 nm.
[c]Assayed by chiral HPLC.

Example 5

Synthesis of 1-(3-ethoxy-4-methoxyphenyl)-2-(methylsulfonyl)ethenamine hydrochloride

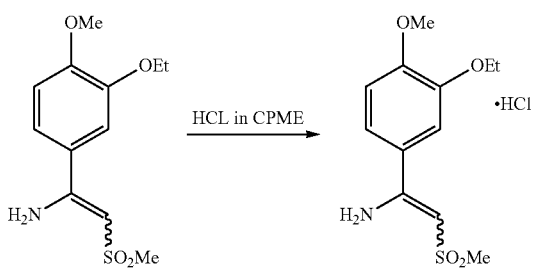 [SMILES: CCOc1cc(C(N)=CS(C)(=O)=O)ccc1OC ; CCOc1cc(C(N)=CS(C)(=O)=O)ccc1OC ; Cl]

1-(3-Ethoxy-4-methoxyphenyl)-2-(methylsulfonyl)ethenamine (1.3 g, 4.79 mmol) was dissolved in 15 mL of CH₂Cl₂ and a 3M solution of hydrogen chloride in cyclopentyl methyl ether (2.5 ml, 7.50 mmol) was added. The mixture was stirred at room temperature for 1 h and filtered. The solids were rinsed with additional CH₂Cl₂ (5 mL) and dried under vacuum, to provide the hydrochloride salt as a pale yellow solid (1.45 g, 98% yield); ¹H NMR (Pyridine-d₅) δ 1.28 (t, J=7.0 Hz, 3H), 3.22 (s, 3H), 3.75 (s, 3H), 3.88 (q, J=6.9 Hz, 2H), 5.53 (s, 1H), 6.99 (d, J=8.5 Hz, 1H), 7.36 (d, J=2.1 Hz, 1H), 7.43 (dd, J=2.2, 8.4 Hz, 1H), 8.32 (br, 3H).

Example 6

Selected Ligands for Asymmetric Hydrogenation of Enamine Hydrochloride

For each reaction, a mixture of bis(1,5-cyclooctadiene)rhodium(I) trifluoromethanesulfonate (7.9 mg, 0.018 mmol), 2,2,2-trifluoroethanol (3 mL), and the appropriate ligand (0.032 mmol) or a preformed complex of the ligand and metal (0.016 mmol) was prepared under nitrogen. Then, 1-(3-ethoxy-4-methoxyphenyl)-2-(methylsulfonyl)ethenamine hydrochloride (100 mg, 0.33 mmol) was added. The resultant mixture was heated to 50° C. and hydrogenated under 90 psig hydrogen pressure. After 18 h, the mixture was removed from the hydrogenator and monitored for conversion by achiral HPLC (Hypersil BDS C₈, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min). Reactions containing >2 Area % of the product enamine were also assayed for chiral purity by chiral HPLC (Chiralpak AD-H 5.0 μm Daicel, 250×4.6 mm, 1.0 mL/min, 280 nm, 70:30:0.1 heptane-i-PrOH-diethylamine or 50:40:10:0.1 heptane-EtOH-i-PrOH-diethylamine). The results are shown in Table 2.

TABLE 2

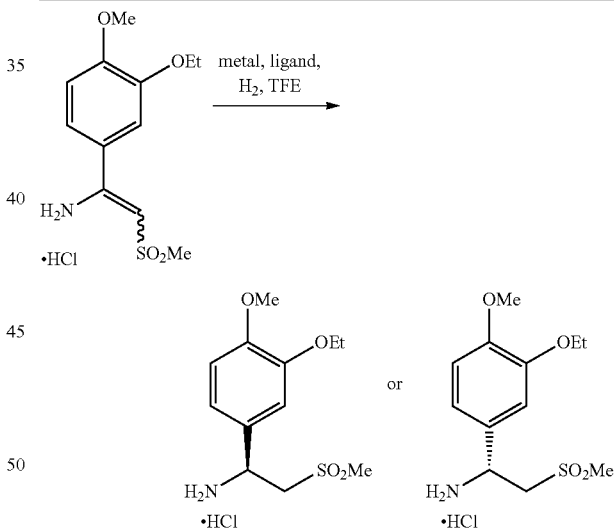

Asymmetric hydrogenation of enamine hydrochloride[a]

| entry | metal and ligand | aminosulfone A%[b] | % ee[b] | configuration |
|---|---|---|---|---|
| 1 | (S,R)-t-Bu Josiphos/[Rh(cod)₂OTf] | 30 | 10.6 | S |
| 2 | Josiphos SL-J011-2/[Rh(cod)₂OTf] | 7.0 | 27.9 | R |
| 3 | (R)-Phanephos/ [Rh(cod)₂OTf] | 4.7 | 35.9 | R |

[a]Reaction conditions: in 30 Vol. 2,2,2-trifluoroethanol (TFE), S/C = 20, 2:1 ligand/metal, 90 psig H₂, 50° C., 18 h.
[b]Area % observed in achiral HPLC with detector set to 278 nm.
[c]Assayed by chiral HPLC.

Example 7

Synthesis of N-(1-(3-ethoxy-4-methoxyphenyl)-2-methylsulfonyl)vinyl)-2,2,2-trifluoroacetamide

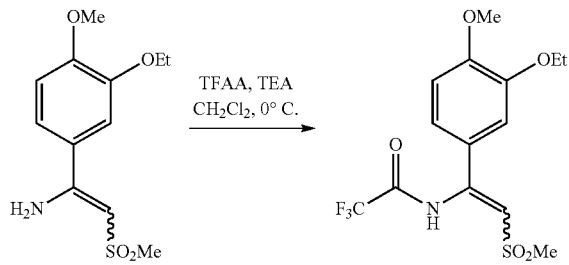 [SMILES: CCOc1cc(C(N)=CS(C)(=O)=O)ccc1OC ; CCOc1cc(C(=CS(C)(=O)=O)NC(=O)C(F)(F)F)ccc1OC]

A solution of 1-(3-ethoxy-4-methoxyphenyl)-2-(methylsulfonyl)ethenamine (2 g, 7.37 mmol) in methylene chloride (20 ml) was cooled on ice, and then 2,2,2-trifluoroacetic anhydride (1.127 mL, 8.11 mmol) was added followed by triethylamine (1.229 mL, 8.85 mmol). The mixture was stirred and allowed to warm to room temperature over 2 h. The mixture was evaporated and the residue was loaded directly onto a silica gel column, eluting with a hexanes-ethyl acetate gradient. The appropriate fractions were pooled and evaporated under vacuum, and the residue was slurried with heptane (40 mL). After 1 h, the solids were filtered washed with additional heptane (25 mL), and dried under vacuum, to afford the product as a white solid (2.3 g, 85% yield); HPLC (Waters BEH $C_{18}$, 1.7 μm, 2.1×50 mm, 0.8 mL/min, 240 nm, 5/95 gradient to 85/15 $CH_3CN$ 0.1% $FA/H_2O$ 0.1% FA in 5 min then 85/15 $CH_3CN$ 0.1% $FA/H_2O$ 0.1% FA for 1 min): 2.03 (5.71%), 2.26 (94.29%); $^1H$ NMR (DMSO-$d_6$) δ 1.35 (t, 3H), 3.12 (s, 3H), 3.81 (s, 3H), 4.08 (q, J=6.9 Hz, 2H), 7.02-7.14 (m, 2H), 7.14-7.21 (m, 2H), 11.18 (s, 1H).

Example 8

Synthesis of (S)-1-(3-ethoxy-4-methoxyphenyl)-2-(methylsulfonyl)ethanamine

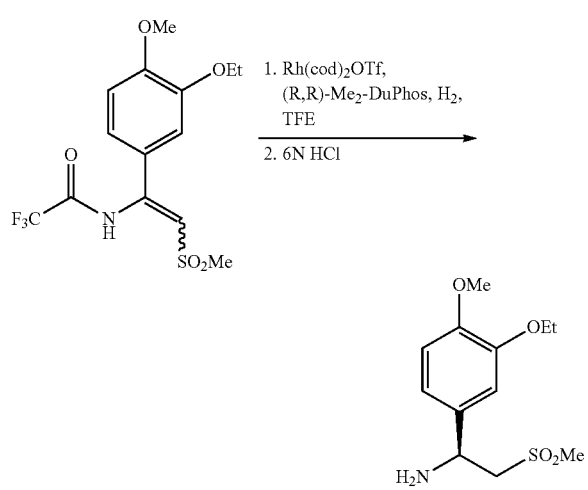

Step 1:

To a solution of bis(1,5-cyclooctadiene)rhodium (I) trifluoromethanesulfonate (0.025 g, 0.054 mmol), 1,2-bis[(2R,5R)-2,5-dimethylphospholano]benzene (0.025 g, 0.082 mmol) in 2,2,2-trifluoroethanol (20 mL) was added N-(1-(3-ethoxy-4-methoxyphenyl)-2-(methylsulfonyl)vinyl)-2,2,2-trifluoroacetamide (1 g, 2.72 mmol). The resulting mixture was hydrogenated at 35° C. under 90 psig hydrogen gas for 18 h. Then, the mixture was cooled to 25° C. and methanol (7 mL) was added dropwise over 15 min, and the mixture was stirred at the same temperature for 2 h. The solids were filtered and rinsed with 1:1 MeOH-TFE (5 mL), and dried under vacuum to provide the reduction product as a white solid (0.47 g, 47% yield); HPLC (Hypersil BDS $C_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min):16.43 (99.5%); $^1H$ NMR (DMSO-$d_6$) δ 1.33 (t, 3H), 2.97 (s, 3H), 3.59-3.79 (m, 5H), 4.02 (q, J=7.0 Hz, 2H), 5.38 (m, J=4.9, 8.8 Hz, 1H), 6.85-6.98 (m, 2H), 7.07 (d, J=1.5 Hz, 1H), 10.03 (d, J=8.5 Hz, 1H).

Step 2:

To the product from Step 1 (0.30 g, 0.81 mmol) was added 6N HCl (15 mL), and the resulting mixture was heated to 85° C. for 16 h, and then cooled to 20° C. The mixture was filtered, and the filtrate was evaporated. The residue was partitioned between 10% $K_2CO_3$ (8 mL) and $CH_2Cl_2$ (8 mL). The lower organic phase was removed and washed with $CH_2Cl_2$ (2×8 mL). To the organic phase was added $CH_2Cl_2$ (25 mL), and the resulting organic phase was washed with 10% $K_2CO_3$ (2×25 mL) and water (25 mL), dried ($MgSO_4$), and evaporated under vacuum. to provide the product as a white solid (150 mg, 68% yield); achiral HPLC (Hypersil BDS $C_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 8.68 (99.5%); chiral HPLC (Chiralpak AD-H 5.0 μm Daicel, 250× 4.6 mm, 1.0 mL/min, 280 nm, 70:30:0.1 heptane-i-PrOH-diethylamine): 7.17 (1.9%), 8.06 (98.1%); $^1H$ NMR (DMSO-$d_6$) δ 1.32 (t, J=7.0 Hz, 3H), 2.08 (s, 2H), 2.96 (s, 3H), 3.23 (dd, J=3.6, 14.4 Hz, 1H), 3.41 (dd, J=9.4, 14.4 Hz, 1H), 3.73 (s, 3H), 4.02 (q, J=7.0 Hz, 2H), 4.26 (dd, J=3.7, 9.3 Hz, 1H), 6.89 (s, 2H), 7.02 (s, 1H); Anal. ($C_{12}H_{19}NO_4S$)C, H, N. Calcd C, 52.73; H, 7.01; N, 5.12. Found C, 53.03; H, 6.78; N, 4.98.

Example 9

Selected Ligands for Asymmetric Hydrogenation of N-Acyl Enamine

For each reaction, a mixture of bis(1,5-cyclooctadiene)rhodium(I) trifluoromethanesulfonate (6.4 mg, 0.014 mmol), 2,2,2-trifluoroethanol (3 mL), and the appropriate ligand (0.027 mmol) or a preformed complex of the ligand and metal (0.014 mmol) was prepared under nitrogen. Then, N-(1-(3-ethoxy-4-methoxyphenyl)-2-(methylsulfonyl)vinyl)-2,2,2-trifluoroacetamide (100 mg, 0.27 mmol) was added. The resultant mixture was heated to 50° C. and hydrogenated under 250 psig hydrogen gas. After 18 h, the mixture was removed from the hydrogenator and monitored for conversion by achiral HPLC (Hypersil BDS $C_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min). Some of the reactions were found to contain aminosulfone as a side product, and the Area % of aminosulfone observed in each reaction is listed in Table 3. Since the starting material N-acyl enamine was found to be moderately labile under the LC conditions, the substrate Area % is provided as the sum of the N-acyl enamine and ketone hydrolysis product Area %. Reactions containing >10 Area % of the product enamine were also assayed for chiral purity by chiral HPLC (Chiralpak AD-H 5.0 μm Daicel, 250×4.6 mm, 1.0 mL/min, 280 nm, 70:30:0.1 heptane-i-PrOH-diethylamine or 50:40:10:0.1 heptane-EtOH-i-PrOH-diethylamine).

TABLE 3

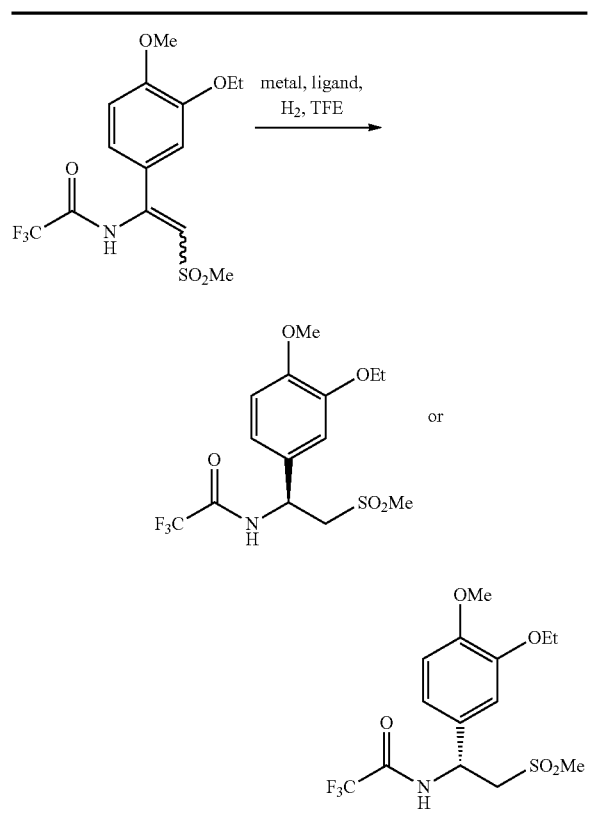

Asymmetric Hydrogenation of N-Trifluoroacetyl Enamine substrate[a]

| entry[a] | metal and ligand | N-acyl aminosulfone A % | N-acyl enamine A %[b] | % ee[c] | configuration |
|---|---|---|---|---|---|
| 1 | (S,R)-t-Bu Josiphos/ [Rh(cod)₂OTf] | 90.16 | 0.51 | 6.3 | S |
| 2 | (S,S)-Methyl-Duphos/ [Rh(cod)₂OTf] | 81.25 | 0.77 | 50.1 | R |
| 3 | (S,S)-Chiraphos/ [Rh(cod)₂OTf] | 85.61 | 4.96 | 9.7 | S |
| 4 | (R)-Phanephos/ [Rh(cod)₂OTf] | 43.25 | 51.36 | 50.7 | R |
| 5 | (S)-(DM-Segphos)/ [Rh(cod)₂OTf] | 87.99 | 6.06 | 9.5 | S |
| 6 | [(R,R)-Me-BPE] Rh(cod)BF₄ | 28.77 | 60.37 | 6.1 | R |
| 7 | (R)-C3-TunePhos/ [Rh(cod)₂OTf] | 91.92 | 2.19 | 11.6 | S |
| 8 | (R)-[Rh(cod)TCFP]BF₄ | 97.37 | 0.43 | 8.6 | R |

[a]Reaction conditions: in 30 Vol. 2,2,2-trifluoroethanol (TFE), S/C = 20, 2:1 ligand/metal, 250 psig H₂, 50° C., 18 h.
[b]Measured as the sum of the trifluoroacetyl enamine Area % and the ketone Area %.
[c]Assayed by chiral HPLC.

Example 10

Asymmetric Reductive Amination of Ketone with Isolation of Enamine

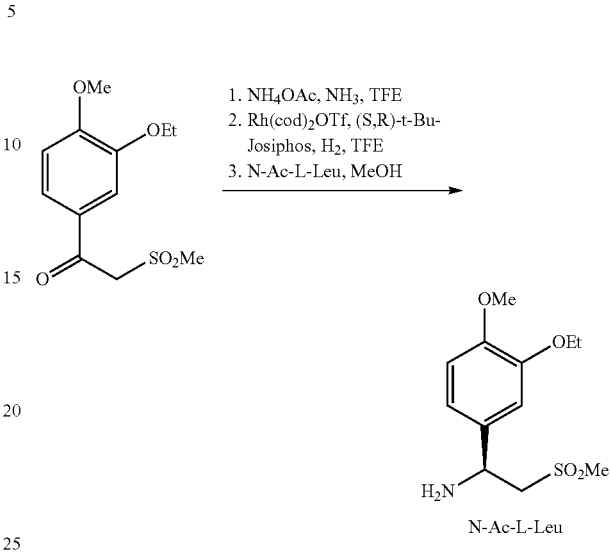

A mixture of 1-(3-ethoxy-4-methoxyphenyl)-2-(methylsulfonyl)ethanone (2 g, 7.34 mmol) and ammonium acetate (0.90 g, 11.7 mmol) in TFE (75 mL) was heated to reflux, and anhydrous ammonia was bubbled through the solution for 45 min while distilling off solvent until the total volume was reduced to 20 mL. Then, the distillation was discontinued and the batch was held at reflux for 24 h. The batch was cooled and evaporated to dryness. Methanol (10 mL) was then added to the residue and the resultant slurry was stirred for 30 min. Then, the solids were filtered, washed with MeOH (5 mL), and dried under vacuum. The solids were then transferred to a hydrogenation reaction vessel. To this vessel was also charged a solution of bis(1,5-cyclooctadiene)rhodium(I) trifluoromethanesulfonate (12.6 mg, 0.027 mmol), (S)-1-[(R)-2-(diphenylphosphino)ferrocenyl]ethyldi-tert-butylphosphine (14.4 mg, 0.027 mmol), and TFE (7.2 mL). The mixture was warmed to 50° C. and hydrogenated under 90 psig hydrogen gas for 18 h. Then Ecosorb C-941 (150 mg) was added and the mixture was stirred at 20° C. for 4 h. The mixture was filtered through Celite and the filtrate was transferred into a clean vessel. The mixture was warmed to 55° C. with stirring, and a solution of N-acetyl-L-leucine (0.79 g, 3.7 mmol) in methanol (7.25 mL) was added over 1 h, resulting in precipitation of the product as the N-acetyl-L-leucine salt. The mixture was stirred at 55° C. for 1 h and then a mixture 1:1 TFE-MeOH (5 mL) was added. The mixture was cooled to 25° C. over 2 h, and stirring proceeded at this temperature for 16 h. The mixture was filtered and washed 1:1 TFE-MeOH (10 mL) and with MeOH (10 mL), and was dried under vacuum. The product was obtained as a white solid (1.35 g, 41% yield); achiral HPLC (Hypersil BDS C₈, 5.0 μm, 250× 4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 8.89 (98.8%); chiral HPLC (Chiralpak AD-H 5.0 μm Daicel, 250×4.6 mm, 1.0 mL/min, 280 nm, 70:30:0.1 heptane-i-PrOH-diethylamine): 6.94 (0.81%), 8.21 (99.34%); ¹H NMR (DMSO-d₆) δ 0.84 (d, 3H), 0.89 (d, J=6.6 Hz, 3H), 1.33 (t, J=7.0 Hz, 3H), 1.41-1.52 (m, 2H), 1.62 (dt, J=6.7, 13.5 Hz, 1H), 1.83 (s, 3H), 2.94 (s, 3H), 3.28 (dd, J=4.0, 14.4 Hz, 1H), 3.44 (dd, J=9.1, 14.4 Hz, 1H), 3.73 (s, 3H), 4.02 (q, J=6.9 Hz, 2H), 4.18 (q, J=7.7 Hz, 1H), 4.29 (dd, J=4.0, 9.1 Hz, 1H), 5.46 (br, 3H), 6.90 (s, 2H), 7.04 (s, 1H), 8.04 (d, J=7.9 Hz, 1H); Anal. ($C_{20}H_{34}N_2O_7S$)C, H, N. Calcd C, 53.79; H, 7.67; N, 6.27. Found C, 53.86; H, 7.97; N, 6.36.

Hz, 1H), 6.89 (s, 2H), 7.02 (s, 1H); Anal. ($C_{12}H_{19}NO_4S$)C, H, N. Calcd C, 52.73; H, 7.01; N, 5.12. Found C, 52.55; H, 7.26; N, 5.25.

Example 11

Asymmetric Reductive Amination of Ketone without Isolation of Enamine

Example 12

Asymmetric Transfer Hydrogenation of Ketone

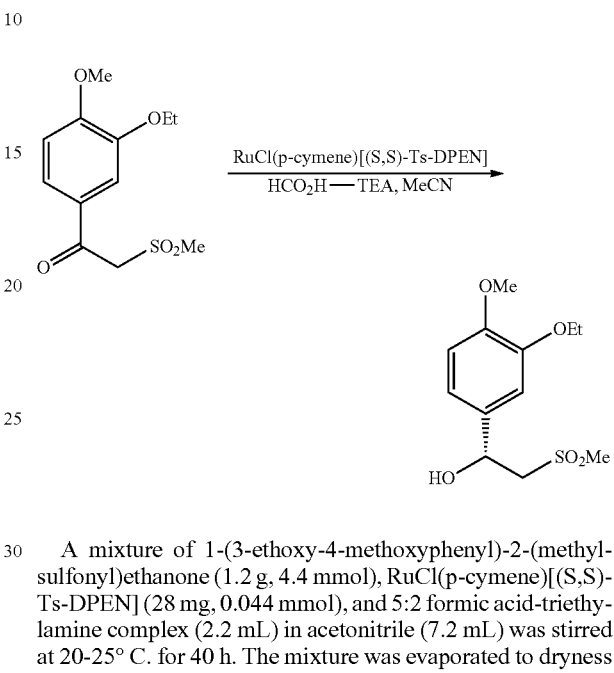

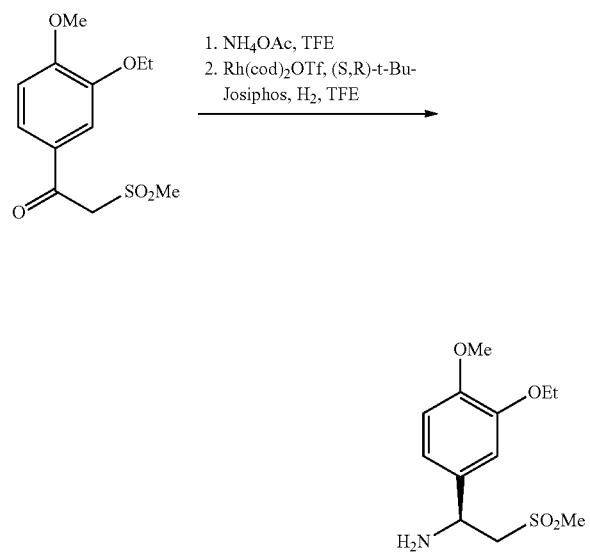

A mixture of 1-(3-ethoxy-4-methoxyphenyl)-2-(methylsulfonyl)ethanone (1.2 g, 4.4 mmol), RuCl(p-cymene)[(S,S)-Ts-DPEN] (28 mg, 0.044 mmol), and 5:2 formic acid-triethylamine complex (2.2 mL) in acetonitrile (7.2 mL) was stirred at 20-25° C. for 40 h. The mixture was evaporated to dryness and the residue was chromatographed on a silica gel column, using a hexanes-ethyl acetate gradient. The appropriate fractions were pooled and evaporated. The residue was triturated with heptane (25 mL) and the resulting slurry was filtered and dried under vacuum to provide (R)-1-(3-ethoxy-4-methoxyphenyl)-2-(methylsulfonyl)ethanol as a white solid (1.05 g, 87% yield); achiral HPLC (Hypersil BDS $C_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 12.37 (99.8%); chiral HPLC (Chiralpak AD-H 5.0 μm Daicel, 250×4.6 mm, 1.0 mL/min, 280 nm, 85:15 heptane-i-PrOH): 18.07 (0.51%), 20.43 (99.4%); $^1$H NMR(CHCl$_3$-d) δ 1.48 (t, J=7.0 Hz, 3H), 2.77 (dd, J=1.1, 2.6 Hz, 1H), 3.05 (s, 3H), 3.17 (dd, J=0.9, 14.7 Hz, 1H), 3.46 (dd, J=10.1, 14.6 Hz, 1H), 3.88 (s, 3H), 4.11 (q, J=7.0 Hz, 2H), 5.27-5.32 (m, 1H), 6.82-6.95 (m, 3H).

A mixture of 1-(3-ethoxy-4-methoxyphenyl)-2-(methylsulfonyl)ethanone (2 g, 7.34 mmol) and ammonium acetate (1.868 g, 24.24 mmol) in TFE (20 mL) was heated to reflux. The batch was slowly distilled, while a solution of NH$_4$OAc (5 g) in TFE (100 mL) was charged at a rate sufficient to maintain a constant volume. When the addition was complete, the mixture was distilled until the total volume was 20 mL. Then, the mixture was cooled to 20° C., and transferred to a hydrogenation reaction vessel. To the mixture was charged bis(1,5-cyclooctadiene)rhodium(I) trifluoromethanesulfonate (0.034 g, 0.073 mmol) and (S)-1-[(R)-2-(diphenylphosphino)ferrocenyl]ethyldi-tert-butylphosphine (0.040 g, 0.073 mmol). The mixture was warmed to 50° C. and hydrogenated under 90 psig hydrogen gas for 18 h. Then, 50 mL water and 5 mL concentrated HCl were added, and the mixture was stirred at 20° C. for 1 h. Then, the mixture was extracted with EtOAc (2×50 mL), and the aqueous phase was made basic with aqueous 10N NaOH until pH~10. The mixture was then extracted with EtOAc (2×50 mL), and the combined organic extracts were dried (MgSO$_4$) and evaporated under vacuum to provide the product as a white solid (0.30 g, 15% yield); achiral HPLC (Hypersil BDS $C_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 8.85 (98.8%); chiral HPLC (Chiralpak AD-H 5.0 μm Daicel, 250×4.6 mm, 1.0 mL/min, 280 nm, 70:30:0.1 heptane-1-PrOH-diethylamine): 7.23 (3.98%), 8.17 (96.02%); $^1$H NMR (DMSO-d$_6$) δ 1.32 (t, J=7.0 Hz, 3H), 2.08 (s, 2H), 2.96 (s, 3H), 3.23 (dd, J=3.6, 14.4 Hz, 1H), 3.41 (dd, J=9.4, 14.4 Hz, 1H), 3.73 (s, 3H), 4.02 (q, J=7.0 Hz, 2H), 4.26 (dd, J=3.7, 9.3

Example 13

Conversion of Chiral Alcohol to Aminosulfone

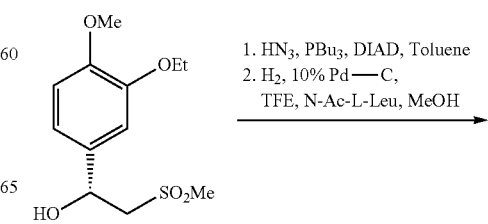

-continued

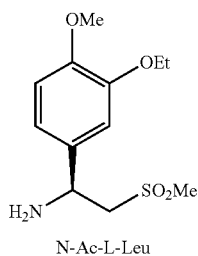

N-Ac-L-Leu

Step 1:

A mixture of (R)-1-(3-ethoxy-4-methoxyphenyl)-2-(methylsulfonyl)ethanol (0.94 g, 3.4 mmol) in toluene (280 mL) and THF (20 mL) was sparged with nitrogen for 15 min, and then a ~1.1 M solution of hydrazoic acid in toluene (13.8 mL, ~15 mmol) was added. The flask was cooled in a dry ice-acetone bath. When the internal temperature reached <−60° C., tributylphosphine (1.7 mL, 6.9 mmol), and then diisopropyl azodicarboxylate (1.6 mL, 7.9 mmol) were added. The cooling bath was charged with dry ice for the next 4 h in order to maintain the reaction temperature at <−60° C., and then the temperature was allowed to gradually rise. After 16 h, the internal temperature had climbed to −2° C. Then, silica gel (20 g) was added and the resulting slurry was evaporated. The residue was chromatographed on a silica gel column, using a hexanes-EtOAc gradient. After pooling and evaporating the appropriate fractions, the residue was triturated with heptane (25 mL) and the slurry was filtered. Solids were dried under vacuum, to provide (S)-4-(1-azido-2-(methylsulfonyl)ethyl)-2-ethoxy-1-methoxybenzene as a white solid (0.84 g, 81% yield); HPLC (Hypersil BDS $C_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 17.77 (99.9%); $^1$H NMR (DMSO-$d_6$) δ 1.33 (t, 3H), 2.99 (s, 3H), 3.55 (dd, J=4.0, 14.7 Hz, 1H), 3.77 (s, 3H), 3.90 (dd, J=9.6, 14.7 Hz, 1H), 3.98-4.13 (m, 2H), 5.01-5.21 (m, 1H), 6.90-7.05 (m, 2H), 7.08 (s, 1H).

Step 2:

The product from Step 1 (0.5 g, 1.670 mmol) was dissolved in TFE, and then 10% Pd—C (0.05 g) was added. The resulting mixture was hydrogenated at ambient temp under 40 psig hydrogen for 9 h, and then the mixture was filtered through Celite. The filtrate was warmed to 55° C. with stirring, and a solution of N-Acetyl-L-Leu (0.29 g, 1.67 mmol) in MeOH (10 mL) was added to the mixture in dropwise fashion over 1 h. The mixture was stirred at the same temperature for 2 h and was then cooled to 21° C. over 2 h and stirred at this temperature for 16 h. The mixture was filtered and rinsed with 1:1 (v/v) TFE-MeOH (10 mL), and the solids were dried under vacuum to provide (S)-1-(3-ethoxy-4-methoxyphenyl)-2-(methylsulfonyl)ethanamine N-acetyl-L-leucine salt as a white solid (0.33 g, 44% yield); achiral HPLC (Hypersil BDS $C_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 7.26 (99.8%); chiral HPLC (Chiralpak AD-H 5.0 µm Daicel, 250×4.6 mm, 1.0 mL/min, 280 nm, 70:30:0.1 heptane-i-PrOH-diethylamine): 7.10 (2.8%), 8.02 (97.2%); $^1$H NMR (DMSO-$d_6$) δ 0.84 (d, 3H), 0.89 (d, J=6.6 Hz, 3H), 1.33 (t, J=7.0 Hz, 3H), 1.41-1.52 (m, 2H), 1.62 (dt, J=6.7, 13.5 Hz, 1H), 1.83 (s, 3H), 2.94 (s, 3H), 3.28 (dd, J=4.0, 14.4 Hz, 1H), 3.44 (dd, J=9.1, 14.4 Hz, 1H), 3.73 (s, 3H), 4.02 (q, J=6.9 Hz, 2H), 4.18 (q, J=7.7 Hz, 1H), 4.29 (dd, J=4.0, 9.1 Hz, 1H), 5.46 (br, 3H), 6.90 (s, 2H), 7.04 (s, 1H), 8.04 (d, J=7.9 Hz, 1H).

Example 14

Selected Ligands for Asymmetric Hydrogenation Using Hydrogen Gas

For each reaction, a mixture of 1-(3-ethoxy-4-methoxyphenyl)-2-(methylsulfonyl)ethanone (300 mg, 1.1 mmol), and a preformed complex of ligand and metal (0.011 mmol) in the indicated solvent (3 mL) was assembled under an inert atmosphere. In some cases as indicated in Table 4 below, a 1.0 M of t-BuOK in t-butanol (0.11 mL, 0.11 mmol) was added. The resultant mixture was heated to 50° C. and hydrogenated under 450 psig hydrogen gas. After 18 h, the mixture was monitored for conversion by achiral HPLC (Hypersil BDS $C_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min). Reactions containing >~10 Area % of the product enamine were also assayed for chiral purity by chiral HPLC (Chiralpak AD-H 5.0 µm Daicel, 250×4.6 mm, 1.0 mL/min, 280 nm, 70:30:0.1 heptane-i-PrOH-diethylamine or 50:40:10:0.1 heptane-EtOH-i-PrOH-diethylamine).

TABLE 4

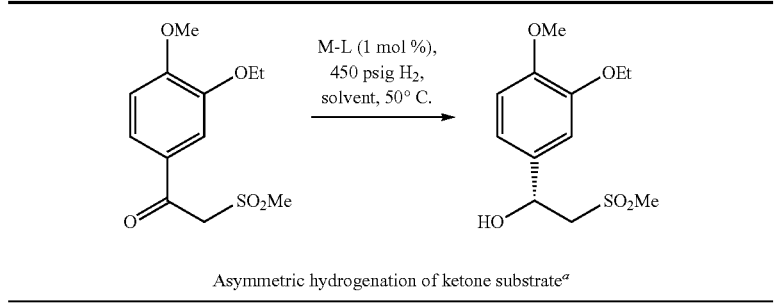

Asymmetric hydrogenation of ketone substrate[a]

| Entry | M-L | Solvent | Additive | Ketone A %[b] | Alcohol A %[b] | ee[c] |
|---|---|---|---|---|---|---|
| 1 | (S)-Ru(OAc)$_2$(BINAP) | TFE | — | 87.27 | 12.37 | 28.5% |
| 2 | (S)-Ru(OAc)$_2$(BINAP) | TFE | t-BuOK | 66.46 | 32.81 | 23.3% |
| 3 | (S)-Ru(OAc)$_2$(DM-SEGPHOS) | TFE | — | 77.32 | 22.17 | 36.2% |
| 4 | RuCl(p-cymene)[(S,S)-Ts-DPEN] | i-PrOH | t-BuOK | 23.00 | 74.43 | 82.0% |

| 5 | RuCl(p-cymene)[(S,S)-Ts-DPEN] | TFE | | 42.45 | 57.17 | 66.9% |
| 6 | RuCl$_2$[(R)-(DM-SEGPHOS)][(R,R)-(DPEN)] | i-PrOH | t-BuOK | 16.24 | 61.80 | 63.1% |

$^a$Reaction conditions: in 10 Vol. of the indicated solvent, S/C = 100, 450 psig H$_2$, 50° C., 18 h.
$^b$Area % observed in achiral HPLC with detector set to 278 nm.
$^c$Assayed by chiral HPLC.

Example 15

Asymmetric Hydrogenation of Ketone

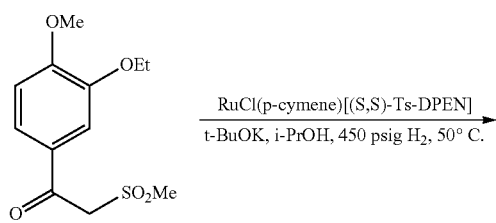

A 1.0M t-BuOK solution in 2-methyl-2-propanol (0.220 mL, 0.220 mmol) was diluted into 2-propanol (12 mL). To the resulting solution was added RuCl(p-cymene)[(S,S)-Ts-DPEN] (28 mg, 0.044 mmol) and 1-(3-ethoxy-4-methoxyphenyl)-2-(methylsulfonyl)ethanone (1.2 g, 4.4 mmol). The mixture was hydrogenated at 50° C. under 450 psig hydrogen gas for 16 h. Then, the mixture was evaporated. The residue was dissolved in CH$_2$Cl$_2$ (50 mL), and this solution was washed with 1N NaOH (2×50 mL), water (50 mL) and brine (50 mL). The organic phase was evaporated and the residue was loaded directly onto a silica gel column, using a hexanes-ethyl acetate gradient. The appropriate fractions were pooled and evaporated. The residue was slurried with MTBE (20 mL) for 1 h and filtered. The filter was washed with MTBE (5 mL) and the solids were dried under vacuum to afford (R)-1-(3-ethoxy-4-methoxyphenyl)-2-(methylsulfonyl)ethanol as a white solid (0.63 g, 52% yield); achiral HPLC (Hypersil BDS C$_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 11.38 (99.7%); chiral HPLC (Chiralpak AD-H 5.0 μm Daicel, 250×4.6 mm, 1.0 mL/min, 280 nm, 85:15 heptane-i-PrOH): 17.77 (9.1%), 20.14 (90.9%).

Example 16

Asymmetric Reduction of Enamine with Aminoindanol/Borane

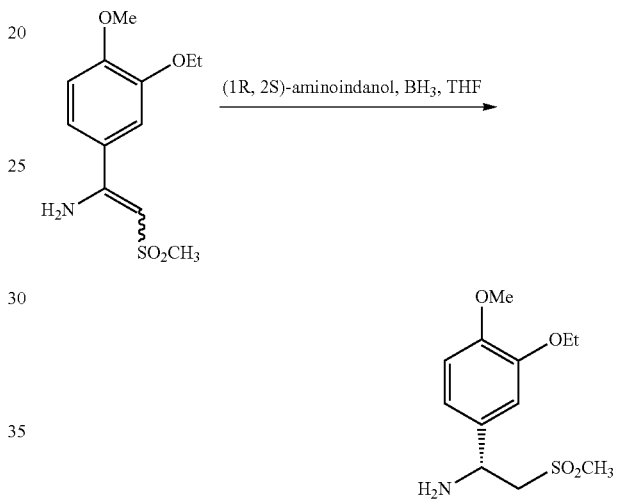

A mixture of (1R,2S)-aminoindanol (3.8 g, 25.5 mmol) and THF (65 mL) was stirred at 15-20° C. and borane diethylaniline (7.4 g, 45.4 mmol, 1.8 eq) was added over approximately 5 minutes. The mixture was cooled to −3° C. and 1-(3-ethoxy-4-methoxyphenyl)-2-(methylsulfonyl)ethenamine (6.9 g, 25.5 mmol) was added over 72 h. 7% HCl (120 mL) was added to the mixture at 0-10° C. The mixture was warmed to 15° C. and was washed with ethyl acetate (100 mL). The aqueous layer was adjusted to pH 10 using with 4% aqueous sodium hydroxide, and the resulting mixture was extracted with methylene chloride (2×300 mL). The combined organic layers were concentrated at reduced pressure to give 14.2 g of a crude white solid. This solid was slurried in heptanes (200 ml) and filtered, to afford 6.4 g of a white solid. This material was purified by flash column chromatography eluting with 10% methanol in ethyl acetate, providing 3.4 g, in 49% yield, as a white solid. achiral HPLC (Hypersil BDS C$_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 9.21 (>99.9%); chiral HPLC (Chiralpak AD-H 5.0 μm Daicel, 250×4.6 mm, 1.0 mL/min, 280 nm, 70:30:0.1 heptane-i-PrOH-diethylamine): 7.43 (64.02%), 8.52 (35.98%); $^1$H NMR (DMSO-d$_6$) δ 1.32 (t, J=7.0 Hz, 3H), 2.08 (s, 2H), 2.96 (s, 3H), 3.23 (dd, J=3.6, 14.4 Hz, 1H), 3.41 (dd, J=9.4, 14.4 Hz, 1H), 3.73 (s, 3H), 4.02 (q, J=7.0 Hz, 2H), 4.26 (dd, J=3.7, 9.3 Hz, 1H), 6.89 (s, 2H), 7.02 (s, 1H).

What is claimed is:

1. A process for preparing an enantiomerically enriched compound of Formula (I):

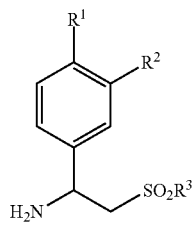

or a salt, solvate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, or $(C_3-C_{18})$cycloalkyl-$(C_1-C_6)$alkoxy, or an isotopologue thereof; and $R^3$ is $(C_1-C_6)$alkyl, or an isotopologue thereof; comprising the step of reducing an enamine of Formula (II):

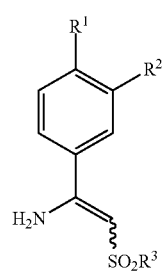

or a salt or isotopologue thereof, via hydrogenation in the presence of (1) a metal catalyst and a chiral ligand, or (2) a chiral metal catalyst/ligand complex to form the compound of Formula (I) with an enantiomeric excess of at least 10%.

2. The process of claim 1, wherein $R^1$ and $R^2$ are substituted or unsubstituted $(C_1-C_6)$alkoxy, or an isotopologue thereof.

3. The process of claim 2, wherein $R^1$ is OMe, or an isotopologue thereof, $R^2$ is OEt, or an isotopologue thereof, and $R^3$ is Me, or an isotopologue thereof.

4. The process of claim 1, wherein the metal catalyst contains rhodium.

5. The process of claim 4, wherein the metal catalyst is $Rh(cod)_2OTf$.

6. The process of claim 1, wherein the chiral ligand or chiral metal catalyst/ligand complex is (S, R)-t-Bu Josiphos, Josiphos SL-J011-2, (S,S)-Me-Duphos, (S,S)-Chiraphos, (R)-Phanephos, (R)—Ru(OAc)$_2$(DM-segphos), [(R,R)-Me-BPE]Rh(cod)BF$_4$, (R)—C$_3$-TunePhos, (R)-[Rh(cod)TCFP]BF$_4$, or a stereoisomer thereof.

7. The process of claim 6, wherein the chiral ligand is (S, R)-t-Bu Josiphos.

8. The process of claim 1, wherein the load of catalyst is between about 0.05 mol % and about 5 mol %.

9. The process of claim 1, wherein the molar ratio of the chiral ligand to the metal catalyst is from about 3:1 to about 1:1.

10. The process of claim 1, wherein the hydrogen pressure is between about 15 psig and about 250 psig.

11. The process of claim 1, wherein the solvent is ethyl acetate, diethyl ether, tetrahydrofuran, 1,4-dioxane, acetonitrile, dichloromethane, chloroform, N-methyl pyrrolidinone, dimethyl formamide, dimethyl sulfoxide, formic acid, acetic acid, methanol, ethanol, isopropanol, 2,2,2-trifluoroethanol, or mixtures thereof.

12. The process of claim 11, wherein the solvent is 2,2,2-trifluoroethanol.

13. The process of claim 1, wherein the reaction temperature is about 50° C.

14. The process of claim 1, wherein the compound of Formula (I) is formed with an enantiomeric excess of at least 25%.

15. The process of claim 1, wherein the compound of Formula (I) is formed with an enantiomeric excess of at least 85%.

16. The process of claim 1, wherein the compound of Formula (I) is formed with an enantiomeric excess of at least 95%.

17. The process of claim 1, wherein the compound of Formula (I) is formed with at least 75% by weight of one enantiomer.

18. The process of claim 1, wherein the compound of Formula (I) is formed with at least 85% by weight of one enantiomer.

19. The process of claim 1, wherein the compound of Formula (I) is formed with at least 95% by weight of one enantiomer.

20. A process for preparing a compound of Formula (I):

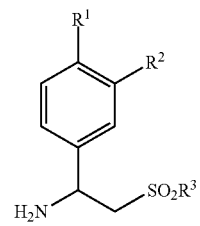

or a salt, solvate, isotopologue, or polymorph thereof, wherein $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, or $(C_3-C_{18})$cycloalkyl-$(C_1-C_6)$alkoxy, or an isotopologue thereof; and $R^3$ is $(C_1-C_6)$alkyl, or an isotopologue thereof;

comprising the steps of
(a) reacting a ketone of Formula (V):

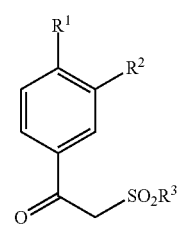

or an isotopologue thereof, with ammonia or an ammonium salt to form an enamine of Formula (II):

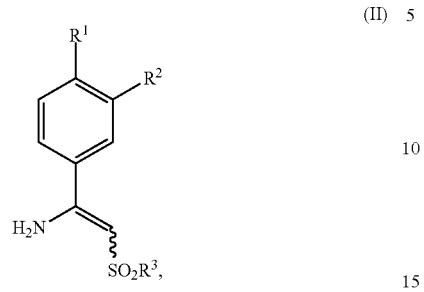

(II)

or a salt or isotopologue thereof;

(b) optionally isolating the enamine of Formula (II), or a salt or isotopologue thereof; and (c) reducing the enamine of Formula (II), or a salt or isotopologue thereof, via hydrogenation in the presence of (1) a metal catalyst and a chiral ligand, or (2) a chiral metal catalyst/ligand complex.

21. The process of claim 20, wherein $R^1$ and $R^2$ are substituted or unsubstituted ($C_1$-$C_6$)alkoxy, or an isotopologue thereof.

22. The process of claim 21, wherein $R^1$ is OMe, or an isotopologue thereof, $R^2$ is OEt, or an isotopologue thereof, and $R^3$ is Me, or an isotopologue thereof.

23. The process of claim 20, wherein the ammonium salt in step (a) is ammonium acetate.

24. The process of claim 20, wherein the metal catalyst in step (c) contains rhodium.

25. The process of claim 24, wherein the metal catalyst in step (c) is Rh(cod)$_2$OTf.

26. The process of claim 20, wherein the chiral ligand or chiral metal catalyst/ligand complex in step (c) is (S, R)-t-Bu Josiphos, Josiphos SL-J011-2, (S,S)-Me-Duphos, (S,S)-Chiraphos, (R)-Phanephos, (R)—Ru(OAc)$_2$(DM-segphos), [(R,R)-Me-BPE]Rh(cod)BF$_4$, (R)—C$_3$-TunePhos, (R)-[Rh(cod)TCFP]BF$_4$, or a stereoisomer thereof.

27. The process of claim 26, wherein the chiral ligand in step (c) is (S,S)-Me-Duphos.

28. The process of claim 20, wherein the load of catalyst in step (c) is between about 0.05 mol % and about 5 mol %.

29. The process of claim 20, wherein the molar ratio of the chiral ligand to the metal catalyst in step (c) is from about 3:1 to about 1:1.

30. The process of claim 20, wherein the hydrogen pressure in step (c) is between about 15 psig and about 250 psig.

31. The process of claim 20, wherein the solvent in step (c) is ethyl acetate, diethyl ether, tetrahydrofuran, 1,4-dioxane, acetonitrile, dichloromethane, chloroform, N-methyl pyrrolidinone, dimethyl formamide, dimethyl sulfoxide, formic acid, acetic acid, methanol, ethanol, isopropanol, 2,2,2-trifluoroethanol, or mixtures thereof.

32. The process of claim 31, wherein the solvent in step (c) is 2,2,2-trifluoroethanol.

33. The process of claim 20, wherein the reaction temperature in step (c) is about 50° C.

34. A process for preparing an enantiomerically enriched compound of Formula (I):

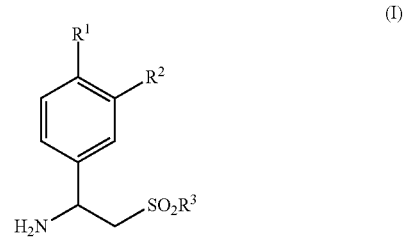

(I)

or a salt, solvate, isotopologue, or polymorph thereof, wherein $R^1$ and $R^2$ are each independently hydrogen, halogen, substituted or unsubstituted ($C_1$-$C_6$)alkyl, substituted or unsubstituted ($C_1$-$C_6$)alkoxy, ($C_3$-$C_{18}$)cycloalkyl, ($C_3$-$C_6$)cycloalkoxy, cyano, —CF$_3$, or ($C_3$-$C_{18}$)cycloalkyl-($C_1$-$C_6$)alkoxy, or an isotopologue thereof; and $R^3$ is ($C_1$-$C_6$)alkyl, or an isotopologue thereof;

comprising the step of reducing an enamine of Formula (II):

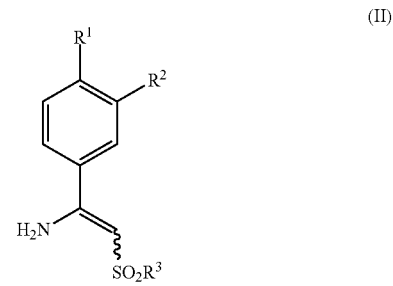

(II)

or a salt or isotopologue thereof, via borane reduction in the presence of a borane reagent and a chiral ligand.

35. The process of claim 34, wherein $R^1$ and $R^2$ are substituted or unsubstituted ($C_1$-$C_6$)alkoxy, or an isotopologue thereof.

36. The process of claim 35, wherein $R^1$ is OMe, or an isotopologue thereof, $R^2$ is OEt, or an isotopologue thereof, and $R^3$ is Me, or an isotopologue thereof.

37. The process of claim 34, wherein the borane reagent is borane N,N-diethylaniline.

38. The process of claim 34, wherein the molar ratio of the compound of Formula (II) to the borane reagent is from about 3:1 to about 1:3.

39. The process of claim 34, wherein the chiral ligand is (1R,2S)-aminoindanol, or a stereoisomer thereof.

40. The process of claim 34, wherein the molar ratio of the compound of Formula (II) to the chiral ligand is from about 3:1 to about 1:3.

41. The process of claim 34, wherein the solvent is ethyl acetate, diethyl ether, tetrahydrofuran, 1,4-dioxane, acetonitrile, dichloromethane, chloroform, N-methyl pyrrolidinone, dimethyl formamide, dimethyl sulfoxide, formic acid, acetic acid, methanol, ethanol, isopropanol, 2,2,2-trifluoroethanol, or mixtures thereof.

42. The process of claim 41, wherein the solvent is tetrahydrofuran.

43. A process for preparing an enantiomerically enriched compound of Formula (I):

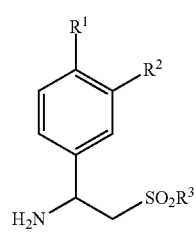

or a salt, solvate, isotopologue, or polymorph thereof, wherein $R^1$ and $R^2$ are each independently hydrogen, halogen, substituted or unsubstituted $(C_1\text{-}C_6)$alkyl, substituted or unsubstituted $(C_1\text{-}C_6)$alkoxy, $(C_3\text{-}C_{18})$cycloalkyl, $(C_3\text{-}C_6)$cycloalkoxy, cyano, —$CF_3$, or $(C_3\text{-}C_{18})$cycloalkyl-$(C_1\text{-}C_6)$alkoxy, or an isotopologue thereof; and $R^3$ is $(C_1\text{-}C_6)$alkyl, or an isotopologue thereof;

comprising the step of reducing an enamine of Formula (II):

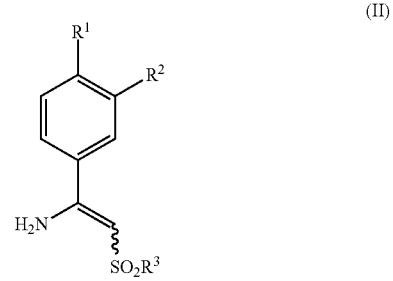

or a salt or isotopologue thereof, via hydrogenation in the presence of (1) a metal catalyst and a chiral ligand, or (2) a chiral metal catalyst/ligand complex, wherein the metal catalyst is $Rh(cod)_2OTf$.

* * * * *